United States Patent
Wolf et al.

(10) Patent No.: US 11,832,876 B2
(45) Date of Patent: *Dec. 5, 2023

(54) TREATING UPPER AIRWAY NERVE TISSUE

(71) Applicant: Aerin Medical Inc., Sunnyvale, CA (US)

(72) Inventors: Scott J. Wolf, Menlo Park, CA (US); Andrew Frazier, Sunnyvale, CA (US)

(73) Assignee: Aerin Medical Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/654,531

(22) Filed: Mar. 11, 2022

(65) Prior Publication Data

US 2022/0265344 A1 Aug. 25, 2022

Related U.S. Application Data

(63) Continuation of application No. 16/815,717, filed on Mar. 11, 2020, now Pat. No. 11,304,746, which is a
(Continued)

(51) Int. Cl.
*A61B 18/14* (2006.01)
*A61B 18/02* (2006.01)
(Continued)

(52) U.S. Cl.
CPC .......... *A61B 18/1485* (2013.01); *A61B 18/02* (2013.01); *A61B 18/082* (2013.01);
(Continued)

(58) Field of Classification Search
CPC .............. A61B 18/1485; A61B 18/082; A61B 2018/00327; A61B 2018/00577;
(Continued)

(56) References Cited

U.S. PATENT DOCUMENTS 4,887,605 A 12/1989 Angelsen et al.
5,348,008 A 9/1994 Bomn et al.
(Continued)

FOREIGN PATENT DOCUMENTS

CN 101325919 12/2008
WO 1999007299 2/1999
(Continued)

OTHER PUBLICATIONS

Extended European Search Report for Application No. 19199126.4, dated Dec. 9, 2019, 6 pages.
(Continued)

*Primary Examiner* — Paula J Stice
(74) *Attorney, Agent, or Firm* — Merchant & Gould P.C.

(57) ABSTRACT

Systems and methods for treating a patient's mucus hypersecretion condition are disclosed herein. Certain implementations may involve a method for reducing mucus secretion in an upper airway of a patient to treat at least one of post nasal drip or chronic cough. The method may include advancing a treatment delivery portion of an energy-based treatment device into a nostril of the patient. The treatment delivery portion may contact mucosal tissue of the upper airway without piercing the mucosal tissue. The treatment delivery portion may deliver treatment to at least one tissue selected from the group of the mucosal tissue and another tissue underlying the mucosal tissue to modify a property of the at least one tissue and thus treat at least one of post nasal drip or chronic cough in the patient.

11 Claims, 30 Drawing Sheets

Related U.S. Application Data continuation of application No. 15/952,985, filed on Apr. 13, 2018, now Pat. No. 10,631,925, which is a continuation of application No. 15/596,195, filed on May 16, 2017, now Pat. No. 9,943,361, which is a continuation of application No. 15/215,762, filed on Jul. 21, 2016, now Pat. No. 9,801,752, which is a continuation of application No. 14/675,689, filed on Mar. 31, 2015, now Pat. No. 9,415,194, which is a continuation-in-part of application No. 14/319,087, filed on Jun. 30, 2014, now Pat. No. 9,072,597, which is a continuation-in-part of application No. 13/495,844, filed on Jun. 13, 2012, now Pat. No. 8,936,594.

(60) Provisional application No. 61/974,534, filed on Apr. 3, 2014, provisional application No. 61/603,864, filed on Feb. 27, 2012, provisional application No. 61/496,930, filed on Jun. 14, 2011.

(51) Int. Cl.
*A61B 18/08* (2006.01)
*A61B 18/16* (2006.01)
*A61B 18/18* (2006.01)
*A61B 18/20* (2006.01)
*A61F 5/08* (2006.01)
*A61M 25/00* (2006.01)
*A61M 25/10* (2013.01)
*A61N 7/02* (2006.01)
*A61B 18/00* (2006.01)

(52) U.S. Cl.
CPC .......... *A61B 18/1442* (2013.01); *A61B 18/16* (2013.01); *A61B 18/1815* (2013.01); *A61B 18/20* (2013.01); *A61F 5/08* (2013.01); *A61M 25/0084* (2013.01); *A61M 25/10* (2013.01); *A61N 7/022* (2013.01); *A61B 2018/00005* (2013.01); *A61B 2018/0022* (2013.01); *A61B 2018/00023* (2013.01); *A61B 2018/00327* (2013.01); *A61B 2018/00577* (2013.01); *A61B 2018/00595* (2013.01); *A61B 2018/00702* (2013.01); *A61B 2018/00821* (2013.01); *A61B 2018/00922* (2013.01); *A61B 2018/00994* (2013.01); *A61B 2018/0225* (2013.01); *A61B 2018/0293* (2013.01); *A61B 2018/143* (2013.01); *A61B 2018/1425* (2013.01); *A61B 2018/1869* (2013.01); *A61M 2025/0091* (2013.01); *A61M 2025/105* (2013.01)

(58) Field of Classification Search
CPC .......... A61B 2018/00595; A61B 2018/00821; A61B 2018/00922; A61B 2018/00214; A61B 2018/00797; A61B 2018/1497; A61F 5/08; A61M 25/10; A61N 1/0546
See application file for complete search history.

(56) References Cited

U.S. PATENT DOCUMENTS

| | | |
|---|---|---|
| 5,533,499 A | 7/1996 | Johnson |
| 5,542,916 A | 8/1996 | Hirsch et al. |
| 5,611,798 A | 3/1997 | Eggers |
| 5,624,439 A | 4/1997 | Edwards et al. |
| 5,674,191 A | 10/1997 | Edwards et al. |
| 5,707,349 A | 1/1998 | Edwards |
| 5,718,702 A | 2/1998 | Edwards |
| 5,728,094 A | 3/1998 | Edwards |
| 5,730,719 A | 3/1998 | Edwards |
| 5,733,280 A | 3/1998 | Avitall |
| 5,738,114 A | 4/1998 | Edwards |
| 5,743,870 A | 4/1998 | Edwards |
| 5,743,904 A | 4/1998 | Edwards |
| 5,746,224 A | 5/1998 | Edwards |
| 5,800,429 A | 9/1998 | Edwards |
| 5,807,306 A | 9/1998 | Shapland et al. |
| 5,816,095 A | 10/1998 | Nordell, II et al. |
| 5,817,049 A | 10/1998 | Edwards |
| 5,820,580 A | 10/1998 | Edwards et al. |
| 5,823,197 A | 10/1998 | Edwards |
| 5,827,277 A | 10/1998 | Edwards |
| 5,843,021 A | 12/1998 | Edwards et al. |
| 5,843,077 A | 12/1998 | Edwards |
| 5,846,235 A | 12/1998 | Pasricha et al. |
| 5,879,349 A | 3/1999 | Edwards |
| 5,938,659 A | 8/1999 | Tu |
| 6,045,549 A | 4/2000 | Smethers et al. |
| 6,096,033 A | 8/2000 | Tu et al. |
| 6,102,907 A | 8/2000 | Smethers et al. |
| 6,109,268 A * | 8/2000 | Thapliyal ........... A61B 18/1485 606/41 |
| 6,126,657 A | 10/2000 | Edwards et al. |
| 6,131,579 A | 10/2000 | Thorson et al. |
| 6,139,546 A | 10/2000 | Koenig et al. |
| 6,152,143 A | 11/2000 | Edwards |
| 6,165,173 A | 12/2000 | Kamdar et al. |
| 6,179,803 B1 | 1/2001 | Edwards et al. |
| 6,210,355 B1 | 4/2001 | Edwards et al. |
| 6,228,079 B1 | 5/2001 | Koenig |
| 6,231,569 B1 | 5/2001 | Bek et al. |
| 6,293,941 B1 | 9/2001 | Strul et al. |
| 6,309,386 B1 | 10/2001 | Bek |
| 6,371,926 B1 | 4/2002 | Thorson et al. |
| 6,383,181 B1 | 5/2002 | Johnston et al. |
| 6,391,028 B1 | 5/2002 | Fanton et al. |
| 6,416,491 B1 | 7/2002 | Edwards et al. |
| 6,416,505 B1 * | 7/2002 | Fleischman ........ A61B 18/1482 606/1 |
| 6,425,151 B2 | 7/2002 | Barnett |
| 6,431,174 B1 | 8/2002 | Knudson et al. |
| 6,451,013 B1 | 9/2002 | Bays et al. |
| 6,502,574 B2 | 1/2003 | Stevens |
| 6,551,310 B1 | 4/2003 | Ganz et al. |
| 6,562,036 B1 | 5/2003 | Ellman et al. |
| 6,575,969 B1 | 6/2003 | Rittman et al. |
| 6,589,235 B2 | 7/2003 | Wong et al. |
| 6,659,106 B1 | 12/2003 | Hovda et al. |
| 6,911,027 B1 | 6/2005 | Edwards et al. |
| 6,978,781 B1 | 12/2005 | Jordan |
| 7,055,523 B1 | 6/2006 | Brown |
| 7,097,641 B1 | 8/2006 | Arless et al. |
| 7,114,495 B2 | 10/2006 | Lockwood, Jr. |
| 7,322,993 B2 | 1/2008 | Metzger et al. |
| 7,361,168 B2 | 4/2008 | Makower |
| 7,416,550 B2 | 8/2008 | Protsenko et al. |
| 7,442,191 B2 | 10/2008 | Hovda et al. |
| 7,655,243 B2 | 2/2010 | Deem et al. |
| 7,678,069 B1 | 3/2010 | Baker et al. |
| 7,780,730 B2 | 8/2010 | Saidi |
| 7,824,394 B2 | 11/2010 | Manstein |
| 7,850,683 B2 | 12/2010 | Elkins et al. |
| 7,997,278 B2 | 8/2011 | Utley et al. |
| 8,114,062 B2 | 2/2012 | Muni et al. |
| 8,128,617 B2 | 3/2012 | Bencini et al. |
| 8,137,345 B2 | 3/2012 | McNall, III et al. |
| 8,317,781 B2 | 11/2012 | Owens et al. |
| 8,317,782 B1 | 11/2012 | Ellman et al. |
| 8,936,594 B2 | 1/2015 | Wolf et al. |
| 8,986,301 B2 | 3/2015 | Wolf et al. |
| 9,027,597 B2 | 5/2015 | Kubo et al. |
| 9,072,597 B2 | 7/2015 | Wolf et al. |
| 9,125,677 B2 | 9/2015 | Sobol et al. |
| 9,179,964 B2 | 11/2015 | Wolf et al. |
| 9,179,967 B2 | 11/2015 | Wolf et al. |
| 9,237,924 B2 | 1/2016 | Wolf et al. |
| 9,247,989 B2 | 2/2016 | Truckai |
| 9,415,194 B2 | 8/2016 | Wolf et al. |
| 9,433,463 B2 | 9/2016 | Wolf et al. |
| 9,452,010 B2 | 9/2016 | Wolf et al. |
| 9,452,087 B2 | 9/2016 | Holm et al. |

(56) References Cited

U.S. PATENT DOCUMENTS

| | | |
|---|---|---|
| 9,486,278 B2 | 11/2016 | Wolf et al. |
| 9,526,571 B2 | 12/2016 | Wolf et al. |
| 9,687,288 B2 | 6/2017 | Saadat |
| 9,687,296 B2 | 6/2017 | Wolf et al. |
| 9,763,723 B2 | 9/2017 | Saadat |
| 9,763,743 B2 | 9/2017 | Lin et al. |
| 9,770,293 B2 | 9/2017 | Dresher |
| 9,788,886 B2 | 10/2017 | Wolf et al. |
| 9,801,752 B2 | 10/2017 | Wolf et al. |
| 9,888,957 B2 | 2/2018 | Wolf et al. |
| 9,913,682 B2 | 3/2018 | Wolf et al. |
| 9,943,361 B2 | 4/2018 | Wolf et al. |
| 10,028,780 B2 | 7/2018 | Wolf et al. |
| 10,028,781 B2 | 7/2018 | Saadat |
| 10,265,115 B2 | 4/2019 | Wolf et al. |
| 10,335,221 B2 | 7/2019 | Wolf et al. |
| 10,376,300 B2 | 8/2019 | Wolf et al. |
| 10,398,489 B2 | 9/2019 | Wolf et al. |
| 10,456,185 B2 | 10/2019 | Wolf et al. |
| 10,456,186 B1 | 10/2019 | Wolf et al. |
| 10,470,814 B2 | 11/2019 | Wolf et al. |
| 10,485,603 B2 | 11/2019 | Wolf et al. |
| 10,603,059 B2 | 3/2020 | Dinger et al. |
| D880,694 S | 4/2020 | Ng et al. |
| D881,904 S | 4/2020 | Angeles et al. |
| 10,631,925 B2 | 4/2020 | Wolf et al. |
| 10,722,282 B2 | 7/2020 | Wolf et al. |
| 10,932,853 B2 | 3/2021 | Wolf et al. |
| 11,033,318 B2 | 6/2021 | Wolf et al. |
| 11,304,746 B2 | 4/2022 | Wolf et al. |
| 2002/0010460 A1 | 1/2002 | Joye |
| 2002/0016588 A1 | 2/2002 | Wong et al. |
| 2002/0049464 A1 | 4/2002 | Donofrio et al. |
| 2002/0087155 A1 | 7/2002 | Underwood et al. |
| 2002/0128641 A1 | 9/2002 | Underwood et al. |
| 2003/0069620 A1* | 4/2003 | Li .................. A61M 25/10 604/103.08 |
| 2003/0144659 A1 | 7/2003 | Edwards |
| 2003/0208194 A1 | 11/2003 | Hovda et al. |
| 2003/0225403 A1 | 12/2003 | Woloszko et al. |
| 2004/0030334 A1 | 2/2004 | Quick |
| 2004/0193238 A1 | 9/2004 | Mosher et al. |
| 2004/0210214 A1 | 10/2004 | Knowlton |
| 2004/0215235 A1 | 10/2004 | Jackson et al. |
| 2004/0220644 A1 | 11/2004 | Shalev et al. |
| 2005/0020901 A1 | 1/2005 | Belson |
| 2005/0119643 A1 | 6/2005 | Sobol et al. |
| 2005/0171522 A1 | 8/2005 | Christopherson |
| 2005/0222565 A1 | 10/2005 | Manstein |
| 2005/0234439 A1 | 10/2005 | Underwood |
| 2005/0234443 A1 | 10/2005 | Rioux |
| 2005/0240147 A1 | 10/2005 | Makower et al. |
| 2005/0288665 A1 | 12/2005 | Woloszko et al. |
| 2006/0190022 A1 | 8/2006 | Beyer |
| 2006/0195169 A1 | 8/2006 | Gross et al. |
| 2006/0235377 A1 | 10/2006 | Earley et al. |
| 2006/0253117 A1 | 11/2006 | Hovda et al. |
| 2006/0276817 A1 | 12/2006 | Vassallo et al. |
| 2007/0043350 A1 | 2/2007 | Soltesz et al. |
| 2007/0049999 A1 | 3/2007 | Esch et al. |
| 2007/0066944 A1 | 3/2007 | Nyte |
| 2007/0073282 A1 | 3/2007 | McGarrigan et al. |
| 2007/0093710 A1 | 4/2007 | Maschke |
| 2007/0219600 A1 | 9/2007 | Gertner et al. |
| 2007/0244529 A1 | 10/2007 | Choi et al. |
| 2008/0004613 A1 | 1/2008 | Barbut |
| 2008/0027423 A1 | 1/2008 | Choi et al. |
| 2008/0027480 A1 | 1/2008 | van der Burg et al. |
| 2008/0082090 A1 | 4/2008 | Manstein |
| 2008/0125626 A1 | 5/2008 | Chang et al. |
| 2008/0154237 A1 | 6/2008 | Chang et al. |
| 2008/0183251 A1 | 7/2008 | Azar et al. |
| 2008/0255642 A1 | 10/2008 | Zarins et al. |
| 2008/0312644 A1 | 12/2008 | Fourkas et al. |
| 2009/0018485 A1 | 1/2009 | Krespi et al. |
| 2009/0124958 A1 | 5/2009 | Li et al. |
| 2009/0143821 A1 | 6/2009 | Stupak |
| 2009/0192505 A1 | 7/2009 | Askew et al. |
| 2009/0292358 A1 | 11/2009 | Saidi |
| 2009/0299355 A1 | 12/2009 | Bencini |
| 2010/0144996 A1 | 6/2010 | Kennedy et al. |
| 2010/0152730 A1 | 6/2010 | Makower et al. |
| 2010/0160906 A1 | 6/2010 | Jarrard |
| 2010/0174283 A1 | 7/2010 | McNall, III et al. |
| 2010/0204560 A1 | 8/2010 | Salahieh et al. |
| 2010/0241112 A1 | 9/2010 | Watson |
| 2010/0260703 A1 | 10/2010 | Yankelson et al. |
| 2011/0009737 A1 | 1/2011 | Manstein |
| 2011/0118726 A1* | 5/2011 | De La Rama ..... A61B 18/1492 606/41 |
| 2011/0130689 A1* | 6/2011 | Cohen ................ A61B 18/1477 601/3 |
| 2011/0180064 A1 | 7/2011 | Tanaka et al. |
| 2011/0282268 A1 | 11/2011 | Baker et al. |
| 2011/0288477 A1 | 11/2011 | Ressemann et al. |
| 2011/0301587 A1 | 12/2011 | Deem et al. |
| 2012/0029512 A1 | 2/2012 | Willard |
| 2012/0039954 A1 | 2/2012 | Cupit et al. |
| 2012/0078377 A1 | 3/2012 | Gonzales et al. |
| 2012/0179154 A1 | 7/2012 | Goldberg |
| 2012/0265188 A1 | 10/2012 | Buchbinder et al. |
| 2012/0298105 A1 | 11/2012 | Osorio |
| 2012/0310233 A1 | 12/2012 | Dimmer |
| 2012/0316473 A1 | 12/2012 | Bonutti et al. |
| 2012/0316557 A1 | 12/2012 | Sartor et al. |
| 2012/0323227 A1 | 12/2012 | Wolf et al. |
| 2012/0323232 A1 | 12/2012 | Wolf et al. |
| 2013/0116679 A1 | 5/2013 | Van der Weide et al. |
| 2013/0158536 A1 | 6/2013 | Bloom |
| 2013/0218158 A1 | 8/2013 | Danek et al. |
| 2014/0088463 A1 | 3/2014 | Wolf et al. |
| 2014/0114233 A1 | 4/2014 | Deem et al. |
| 2015/0164571 A1 | 6/2015 | Saadat |
| 2015/0202003 A1 | 7/2015 | Wolf et al. |
| 2016/0045277 A1 | 2/2016 | Lin |
| 2016/0121112 A1 | 5/2016 | Azar |
| 2017/0231651 A1 | 8/2017 | Dinger et al. |
| 2017/0252089 A1 | 9/2017 | Hester |
| 2018/0103940 A1 | 4/2018 | Shin et al. |
| 2018/0177542 A1 | 6/2018 | Wolf et al. |
| 2018/0177546 A1 | 6/2018 | Dinger et al. |
| 2018/0228533 A1 | 8/2018 | Wolf et al. |
| 2018/0263678 A1 | 9/2018 | Saadat |
| 2018/0317997 A1 | 11/2018 | Dinger et al. |
| 2018/0333195 A1 | 11/2018 | Greep et al. |
| 2018/0344378 A1 | 12/2018 | Wolf et al. |
| 2019/0076185 A1 | 3/2019 | Dinger et al. |
| 2019/0201069 A1 | 7/2019 | Wolf et al. |
| 2019/0231409 A1 | 8/2019 | Wolf et al. |
| 2019/0282289 A1 | 9/2019 | Wolf et al. |
| 2019/0336196 A1 | 11/2019 | Wolf et al. |
| 2019/0343577 A1 | 11/2019 | Wolf et al. |
| 2020/0100829 A1 | 4/2020 | Wolf et al. |
| 2020/0129223 A1 | 4/2020 | Angeles et al. |
| 2020/0170699 A1 | 6/2020 | Wolf et al. |

FOREIGN PATENT DOCUMENTS

| | | |
|---|---|---|
| WO | 2001043653 | 6/2001 |
| WO | 2003024349 | 3/2003 |
| WO | 2007037895 | 4/2007 |
| WO | 2007134005 | 11/2007 |
| WO | 2010077980 | 7/2010 |
| WO | 2012174161 | 12/2012 |
| WO | 2013028998 | 2/2013 |
| WO | 2014022436 | 2/2014 |
| WO | 2015047863 | 4/2015 |
| WO | 2015048806 | 4/2015 |
| WO | 2015153696 | 10/2015 |

(56) References Cited

OTHER PUBLICATIONS

Buckley et al., "High-resolution spatial mapping of shear properties in cartilage," J Biomech., Mar. 3, 2010;43 (4)1796-800, Epub Nov. 5, 2009.
Buckley et al., "Mapping the depth dependence of shear properties in articular cartilage," J Biomech., 41 (11)12430-2437, Epub Jul. 10, 2008.
Chen et al., China Journal of Endoscopy, vol. 11, No. 3. pp. 239-243, Mar. 2005, [English Translation of Title] "Radiofrequency treatment of nasal posterior-under nerve ethmoidal nerve and infraturbinal for perennial allergic rhinitis under nasal endoscope," [also translated as] "Preliminary exploration of radiofrequency thermocoagulation of the posterior inferior nasal nerve, anterior ethmoidal nerve, and inferior nasal concha under nasal endoscopy in the treatment of perennial allergic rhinitis." 9 pages.
Cole, "Biophysics of nasal airflow: a review," Am J Rhinol., 14(4):245-249, Jul.-Aug. 2000.
Cole, "The four components of the nasal valve," Am J Rhinol., 17(2):107-110, Mar.-Apr. 2003.
Fang et al., J First Mil Med Univ, vol. 25 No. 7, pp. 876-877, 2005, [English translation of title] "Nasal endoscopy combined with multiple radiofrequency for perennial allergic rhinitis" [also translated as] "Nasal Endoscopic Surgery Combined with Multisite Radiofrequency Technology for Treating Perennial Allergic Rhinitis," 4 pages.
Griffin et al., "Effects of enzymatic treatments on the depth-dependent viscoelastic shear properties of articular cartilage," J Orthop Res., 32(12):1652-1657, Epub Sep. 5, 2014.
International Search Report and Written Opinion for PCT/US2012/042316, dated Aug. 24, 2012, 15 pages.
International Search Report and Written Opinion for PCT/US2014/054726, dated Dec. 23, 2014, 5 pages.
International Search Report and Written Opinion for PCT/US2015/023742, dated Jun. 29, 2015, 5 pages.
Kjaergaard et al., "Relation of nasal air flow to nasal cavity dimensions," Arch Otolaryngol Head Neck Surg., 135 (6):565-570, Jun. 2009.
Kong et al., Journal of Clinical Otorhinolaryngology, 2005. "Clinical observation on radiofrequency ablation treatment in perennial allergic rhinitis," Retrieved from the Internet: <URL:http://en.cnki.com.cn/Article_en/CJFDTOTAL-LCEH200505015.htm>, 1 page.
Liu et al., China Journal of Endoscopy, vol. 14, No. 11, pp. 1127-1130, Nov. 2008, [English Translation of Title] "Impact of treatment of perennial rhinitis by radiofrequency thermocoagulations to vidian and antirior ethomoidal nerves on mucociliary clearance," [also translated as] "Impact of radiofrequency thermocoagulation of bilateral vidian and anterior ethmoidal nerve cluster regions on nasal mucociliary transport function in perennial allergic rhinitis and asomotor rhinitis " 12 pages.
Search Report in European Application No. 18204723.3 dated Feb. 18, 2019, 8 pages.
Silverberg et al., "Structure-function relations and rigidity percolation in the shear properties of articular cartilage," Biophys J., 107(7):1721-1730, Oct. 7, 2014.
Singapore Search Report for Application Serial No. 201309238-2, dated Apr. 17, 2014, 27 pages.
Stewart et al., "Development and validation of the Nasal Obstruction Symptom Evaluation (NOSE) scale," Otolaryngol Head Neck Surg., 130(2):157-163, Feb. 2004.
Stupak, "A Perspective on the Nasal Valve," Dept. of Otorhinolaryngology, Albert Einstein College of Medicine, Nov. 6, 2009.
Stupak, "Endonasal repositioning of the upper lateral cartilage and the internal nasal valve," Ann Otol Rhinol Laryngol., 120(2):88-94, Feb. 2011.
Supplementary European Search Report for Application No. 15772528, dated Sep. 26, 2017, 7 pages.
Extended European Search Report for App. No. 21172995.9, dated Jul. 9, 2021, 8 pages.

\* cited by examiner

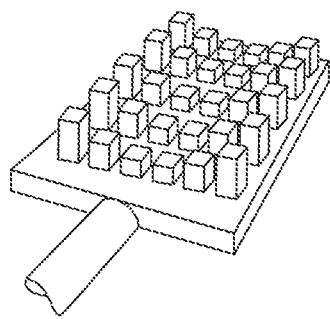 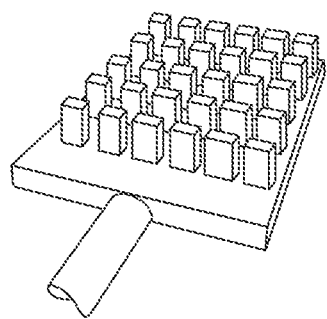 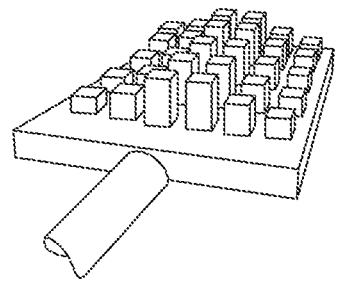
FIG. 26A  FIG. 26B  FIG. 26C
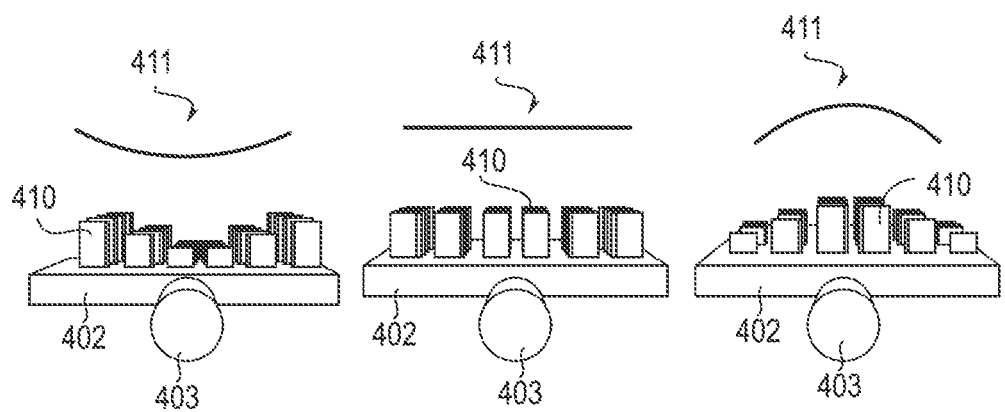
FIG. 26D  FIG. 26E  FIG. 26F

TREATING UPPER AIRWAY NERVE TISSUE

CROSS-REFERENCE TO RELATED APPLICATIONS

This application is a continuation of U.S. patent application Ser. No. 15/952,985, filed Apr. 13, 2018, entitled, "Treating Upper Airway Nerve Tissue," which is a continuation of U.S. patent application Ser. No. 15/596,195, filed May 16, 2017, entitled "Treating Upper Airway Nerve Tissue," which issued on Apr. 17, 2018, as U.S. Pat. No. 9,943,361, which is a continuation of U.S. patent application Ser. No. 15/215,762, filed Jul. 21, 2016, entitled "Post Nasal Drip Treatment," which issued on Oct. 31, 2017, as U.S. Pat. No. 9,801,752, which is a continuation of U.S. patent application Ser. No. 14/675,689, filed Mar. 31, 2015, entitled "Post Nasal Drip Treatment," which issued on Aug. 16, 2016, as U.S. Pat. No. 9,415,194, which claims priority to U.S. Provisional Patent Application No. 61/974,534, filed Apr. 3, 2014, and is also a continuation-in-part of U.S. patent application Ser. No. 14/319,087, filed Jun. 30, 2014, entitled "Methods and Devices to Treat Nasal Airways," which issued on Jul. 7, 2015, as U.S. Pat. No. 9,072,597, which is a continuation-in-part of U.S. patent application Ser. No. 13/495,844, filed Jun. 13, 2012, entitled, "Methods and Devices to Treat Nasal Airways," which issued on Jan. 20, 2015, as U.S. Pat. No. 8,936,594, which claims priority to U.S. Provisional Patent Application No. 61/603,864, filed Feb. 27, 2012, and U.S. Provisional Patent Application No. 61/496,930, filed Jun. 14, 2011. The disclosures of all the above-referenced patent applications are hereby incorporated by reference in their entireties herein.

FIELD

This application relates generally to the field of medical devices and treatments. More specifically, the application relates to systems, devices and methods for treating structures within the upper airway to reduce and/or prevent overproduction and/or flow of mucus to alleviate the discomfort of post nasal drip symptoms.

BACKGROUND OF THE INVENTION

In a healthy human body, glands in the lining of the nose, throat and airways produce about 1 to 1.5 liters daily of a thick, wet substance called mucus. The purpose of mucus is to help trap and destroy harmful bacteria and viruses in the airways before they can enter the body. Mucus produced in the nose is transported toward the throat and into the digestive system. This process is called mucociliary clearance and generally goes unnoticed, similar to breathing or blinking. However, viruses, infections, and the inhalation of airborne irritants, particles and micro-organisms can trigger an overproduction of mucus and/or thicker-than-usual mucus. This increased/thickened mucus causes irritation, which is known as post nasal drip syndrome (PNDS) or upper airway cough syndrome (UACS).

Nasal mucus is produced by the nasal mucosa and mucosal tissues lining airways (trachea, bronchus, bronchioles). Mucosal tissues include specialized airway epithelial cells (goblet cells) and submucosal glands. Goblet cells are situated in the epithelium of the conducting airways, often with their apical surfaces protruding into the lumen, a location which allows them to aid in a rapid response to inhaled airway insults. Goblet cells may have a much greater potential for mucus secretion than do the submucosal glands. Thus, goblet cells may represent the principal frontline defender of the airway.

New information demonstrates that goblet cells can discharge vast quantities of mucus in fractions of a second, a property integral to airway defense against acute insult. Goblet cells can also increase in number in response to continued airway insult. The increase in goblet cells, and hence mucus production, may be a result of hyperplasia (involving cell division) and/or metaplasia (involving cell differentiation). Preventing metaplasia may be achieved by eliminating goblet cell metaplasia inducing components, such as Interleukin (IL)-13. This gene encodes an immunoregulatory cytokine produced primarily by activated Th2 cells. This cytokine is involved in several stages of B-cell maturation and differentiation.

While the overproduction of nasal mucus can be a result of anatomical causes like deviated nasal septum and turbinate hypertrophy, non-anatomical causes, such as allergies, have also been known to trigger PNDS. These patients may have overactive immune systems, leading to an overproduction of mucus. The most straightforward method of treating the allergy problem is to take a test to diagnose the causes of allergies and making lifestyle changes to stay away from these causes. Medications like antihistamines are often prescribed to block allergy mediators. However, antihistamines may thicken mucus secretions and can worsen bacterial rhinitis or sinusitis. A specific antihistamine may lose its effectiveness over time, requiring more or alternative antihistamines to reduce systemic reaction. In addition, antihistamines may come with side effects such as headache, dry mouth, and dry nose.

Nasal-spray corticosteroids (commonly called steroids) are considered the most effective drugs for controlling the symptoms of moderate-to-severe allergic rhinitis. However, side effects may include dryness, burning, stinging in the nasal passage, sneezing, headaches and nosebleed. There may also be long term complications caused by hormone suppression, such as lower resistance to infection, effects on growth in children, nervousness, acne, etc. Cromolyn and leukotriene antagonists may have lesser side effects, but are not as effective as nasal corticosteroids. The major hazard with nasal-delivery decongestants, particularly long-acting forms, is a cycle of dependency and rebound effects. For oral decongestants, side effects such as insomnia, irritability, nervousness, and heart palpitations may be observed.

Immunotherapy (commonly referred to as "allergy shots") is a safe and effective treatment for patients with allergies. The major downside to immunotherapy is that it requires a prolonged course of weekly injections. This makes the treatment process laborious and patients often fail to comply with the regimens, limiting the end results of the therapy.

Therefore, a need exists for a long lasting, single-treatment or low frequency treatment for PNDS caused by allergies, anatomical causes or other causes. Ideally, such a treatment would alleviate PNDS symptoms, without producing severe and/or chronic side effects.

BRIEF SUMMARY

Certain implementations of the systems and methods disclosed herein address the above mentioned needs by delivering a therapy in an upper airway to treat PNDS and/or UACS. The therapy delivered may involve delivering energy to, removing energy from (e.g., cryotherapy) and/or delivering a substance to mucosal tissue and/or a tissue underlying mucosal tissue in the upper airway. The therapy delivery may have any of a number of different effects on the treated tissue. For example, the therapy may decrease the absolute number and/or the mucus producing ability of mucus producing cells and/or mucus glands, such as by inactivating, retarding and/or replacing the cells. In other embodiments, the therapy may ablate or otherwise deactivate nerve tissue underlying mucosal tissue and thus ameliorate PNDS and/or UACS symptoms. In various embodiments, treatment may be applied during early stages of PNDS and/or UACS symptoms, before hyperplasia and metaplasia occur. Such early stage intervention may involve inactivating or modifying goblet cells and/or any other mucus producing cells and/or glands via the application of energy.

Embodiments of the present application are directed to devices, systems and methods for treating upper airways. Such embodiments may be used to treat PNDS by reducing the production of mucus in the upper airways, thus preventing the mucus from causing PNDS. For example, the devices, systems and methods described herein may be used to change the properties of the tissue of the nose and throat, including but not limited to skin, muscle, mucosa, submucosa and nasal turbinate.

According to one embodiment, a device for treating PNDS includes an elongate shaft having a proximal end and a distal end. In one embodiment, the device includes an treatment portion, such as an energy delivery member, sized to be inserted into a nose and/or throat or delivered external to a nose and/or throat. The energy delivery member is configured to deliver energy to tissues within the nose and/or throat and change the properties of a region of the nose and/or throat to minimize mucus production and prevent mucus from causing PNDS. The device may further include a handle at the proximal end of the elongate shaft. The devices described herein may be configured to be positioned internally or externally within the nose, throat and/or mouth. Certain embodiments are configured to be delivered into one or both nostrils, and other embodiments are configured to be delivered into the throat.

Other embodiments of the devices for treating a patient's PNDS include devices that apply other types of treatment. For example, a treatment device may apply energy of form selected from a group consisting of ultrasound, microwave, heat, radiofrequency, electrical, light, cryogenic and laser. The treatment device may also be configured to inject a polymerizing liquid or to deliver cauterizing agent to the upper airway. Other embodiments are described below.

In some embodiments, the device may comprise a treatment element having a shaped surface conformed to the region of the nose or throat to be treated. For embodiments using an energy delivery element, the treatment element may be a separate element from the energy delivery element, or the energy delivery element and the treatment element may be part of the same element. The energy delivery element and/or treatment element in one embodiment may have a concave surface to cover the treatment region as much as possible.

In embodiments using energy delivery, a handle may be provided comprising a button or other input control to activate one or more electrodes. Electrodes may comprise one or more monopolar needles, one or more monopolar plates, or one or more bipolar electrode pairs (which may also comprise one or more needles or plates). These electrodes may be located in various locations, for example, inside the nasal passageway, inside the throat or external to both nose and throat. For example, when using a bipolar electrode pairs, a first electrode surface may be positioned internal to the nose and a second electrode surface may be positioned external to the nose, so that the two electrode surface are positioned on opposite sides of the nasal tissue. In certain implementations, electrodes may be surface acting, transdermal or subdermal (e.g., by access via an incision) or a combination thereof.

The device of one energy delivery embodiment may comprise an adaptor configured to be connected to an energy source, such as a RF energy source. The device may also comprise a control system configured to control the characteristics of the energy applied to the tissue.

A thermocouple or other sensor may be provided to measure a temperature near the tissue or other tissue or device parameter. Sensor(s) to monitor tissue properties such as impedance, resistance, moisture level may also be provided.

In another aspect, a system is provided comprising a device as described above and further below in combination with one or more other components. One such component may be a control system for controlling the energy source and/or treatment device. In another embodiment, the system may comprise a cooling mechanism to cool desired tissue locations while treatment is being applied. In monopolar electrode embodiments, a grounding pad may also be provided as part of the system. Another system includes a positioning and/or other parameters for using the device to treat the feeling and effects of PNDS.

According to another aspect, a method of treating a patient's PNDS is provided. In one embodiment, the method includes altering the tissue properties of the nasal inferior turbinate by applying a treatment sufficient to alter the tissue properties to reduce mucus production.

According to one embodiment, a method of treating a patient's PNDS comprises positioning a treatment element within the upper airway tissue to be treated. The treatment element comprises one or more electrodes, such as described above in further detail below.

In certain implementations, the method may further comprise altering the properties of the nasal or throat tissue by pressing a surface of the treatment element against the upper airway tissue to be treated. In certain implementations, the method may further comprise delivering radiofrequency (RF) energy to the one or more electrodes to locally heat the tissue to be treated, wherein delivering RF energy while altering the properties of the tissue causes less mucus production in the treatment area. The method may also comprise removing the treatment element from the upper airway.

In one aspect, a method for reducing mucus secretion in an upper airway of a patient to treat post nasal drip and/or chronic cough may involve: advancing a treatment delivery portion of an energy-based treatment device into a nostril of the patient; contacting mucosal tissue of the upper airway with the treatment delivery portion, without piercing the mucosal tissue; and delivering a treatment from the treatment delivery portion to the mucosal tissue and/or another tissue underlying the mucosal tissue to modify a property the tissue and thus treat at least one of post nasal drip or chronic cough in the patient.

In some embodiments, the treatment may be delivered without forming an incision in the mucosal tissue and without delivering an implant. In some embodiments, delivering the treatment involves delivering energy from the delivery treatment portion in the form of ultrasound, microwave, heat, radiofrequency, electrical, light or laser energy.

In some embodiments, delivering the treatment comprises delivering radiofrequency energy from a first electrode on a tissue contact surface of the treatment portion across a convex portion of the tissue contact surface to a second electrode on the tissue contact surface. In some embodiments, contacting the mucosal tissue comprises contacting multiple non-piercing bumps on the tissue contact surface with the mucosal tissue. In some embodiments, the at least one tissue comprises nerve tissue underlying the mucosal tissue, and delivering the energy comprises ablating the nerve tissue. Some embodiments may further comprise measuring an amount of delivered energy using a thermocouple on the treatment portion. Some embodiments may further comprise adjusting the amount of delivered energy by adjusting a setting of the treatment delivery portion.

In some embodiments, delivering the treatment comprises removing energy, and the treatment delivery portion comprises a cryotherapy device. In some embodiments, the at least one tissue comprises nerve tissue underlying the mucosal tissue, and removing energy comprises ablating the nerve tissue using the cryotherapy device. In some embodiments, applying a treatment comprises injecting a polymerizing liquid.

In some embodiments, delivering the treatment comprises injuring the at least one tissue. In some embodiments, delivering the treatment comprises injuring goblet cells that are part of the mucosal tissue. In some embodiments, the at least one tissues is selected from the group consisting of cilia, goblet cells, nerves, submucosal tissue, muscle, ligaments, cartilage, tendon, and skin. In some embodiments, delivering the treatment comprises simultaneously mechanically altering the mucosal tissue and delivering energy to the at least one tissue. In some embodiments, delivering the treatment comprises modifying the at least one tissue in a manner that decreases a volumetric rate of mucus production of the mucosal tissue without changing a shape of the mucosal tissue. In some embodiments, delivering the treatment comprises delivering a cauterizing agent to tissue to be treated. In some embodiments, delivering the treatment comprises delivering the treatment to at least one turbinate of the upper airway. In some embodiments, the at least one turbinate comprises an inferior turbinate, and contacting the mucosal tissue comprises contacting a posterior aspect of the inferior turbinate.

In another aspect, a device for reducing mucus secretion in an upper airway of a patient to treat post nasal drip and/or chronic cough may include: an elongate, malleable shaft having a proximal end and a distal end; a handle at the proximal end of the elongate shaft; and a treatment portion at the distal end of the elongate shaft. The treatment portion may include a treatment surface, which may include at least two energy delivery members extending longitudinally along the treatment surface and a concave trough extending longitudinally along the treatment surface and separating the at least two energy delivery members.

In some embodiments, the at least two energy delivery members comprise at least one positive electrode on one side of the concave trough and at least one negative electrode on an opposite side of the concave trough. In some embodiments, the at least one positive electrode comprises a row of positive electrodes, and the at least on negative electrode comprises a row of negative electrodes. In some embodiments, the electrodes (which may be blunt-tipped electrodes) protrude from the treatment surface. Some embodiments further comprise a thermocouple disposed within the concave trough.

In another aspect, a method for reducing mucus secretion in an upper airway of a patient to treat at least one of post nasal drip or chronic cough may involve: bending a malleable shaft of a treatment device into a desired configuration; advancing a treatment portion of the treatment device into a nostril of the patient to contact a treatment surface of the treatment portion with mucosal tissue of the upper airway, without piercing the mucosal tissue; and delivering radiofrequency energy from a first electrode on the treatment surface across a concave trough in the treatment surface to a second electrode on the treatment surface, to treat mucosal tissue and/or another tissue underlying the mucosal tissue to modify a property of the tissue and thus treat post nasal drip and/or chronic cough in the patient. The method also involves measuring an amount of the radiofrequency energy delivered, using a thermocouple disposed in the concave trough, and removing the treatment portion from the upper airway without leaving an implant in the upper airway.

Some embodiments further comprise performing a test to determine whether a desired contact between the treatment surface and the mucosal tissue has been achieved. In some embodiments, delivering and measuring steps comprise delivering a first amount of the radiofrequency energy from the first electrode to the second electrode; measuring a temperature of the mucosal tissue using the thermocouple; and delivering a second amount of the radiofrequency energy from the first electrode to the second electrode, wherein the second amount of radiofrequency energy is based at least in part on the measured temperature.

In some embodiments, the mucosal tissue comprises tissue located on at least one nasal turbinate of the upper airway. In some embodiments, the mucosal tissue comprises tissue located on a posterior aspect of an inferior turbinate. In some embodiments, delivering the radiofrequency energy comprises delivering the radiofrequency energy in an amount that deactivates mucus producing cells by impairing at least one of mucus production ability or cell differentiation ability of the mucus producing cells. In some embodiments, delivering the radiofrequency energy comprises delivering the radiofrequency energy in an amount that causes one or more mucus paths of the upper airway to divert. Some embodiments comprise repeating the bending, advancing, and delivery steps.

These and other aspects and embodiments will be described in further detail below, in reference to the attached drawing figures.

BRIEF DESCRIPTION OF THE DRAWINGS

FIGS. 26A-26F are perspective views of a treatment element with electrodes of adjustable heights according to certain embodiments.

DETAILED DESCRIPTION OF THE INVENTION

The following disclosure provides embodiments of systems and methods for treating PNDS and/or UACS, which may be generally referred to herein as "post-nasal drip" or "PND." Certain embodiments include methods and devices for reshaping, remodeling, strengthening, and/or changing a property and/or type of tissue of the nose and/or upper airway, including but not limited to the epithelial layer, skin, muscle, mucosa, submucosa, and cartilage in the upper airway. Certain embodiments may be used to decrease or eliminate mucus production in the upper airway. While some embodiments may change a property of a tissue, such as an ability of a tissue to produce mucus, other embodiments may change a tissue from one type to another type. One example of this latter change is changing goblet cells to scar tissue. Various embodiments may be used to reduce movement of mucus, reduce amount of mucus produced, reduce frequency of mucus production, change the mucus viscosity/consistency, and/or change the path of mucus flow.

Remodeling or changing the properties of the tissues in the upper airway linings can improve the condition of PND caused by mucus hypersecretion. Methods and devices described herein may be used to treat upper airways without the need for more invasive procedures (e.g., ablation or surgery).

PND symptoms may be alleviated by decreasing mucus production in the upper airways. In certain implementations, mucus production may be decreased by modifying the properties of mucus producing cells in the upper airway epithelium. In some implementations, modifying the properties of the mucus producing cells may include reducing the rate at which cells produce mucus. In some implementations, modifying the properties of mucus producing cells may include deactivating some or all mucus producing cells in a region. Modifying these cells can be performed alone or together with other procedures (e.g., surgical procedures), such as those described above. Such methods and devices may alleviate PND symptoms.

Mucus hypersecretion often occurs when a mucus producing cell displays rapid mucus secretion behavior. To prevent this, properties of the cell can be modified to inactivate or retard the cell so as to halt or impede the release of mucins into the airway.

Figure 1:
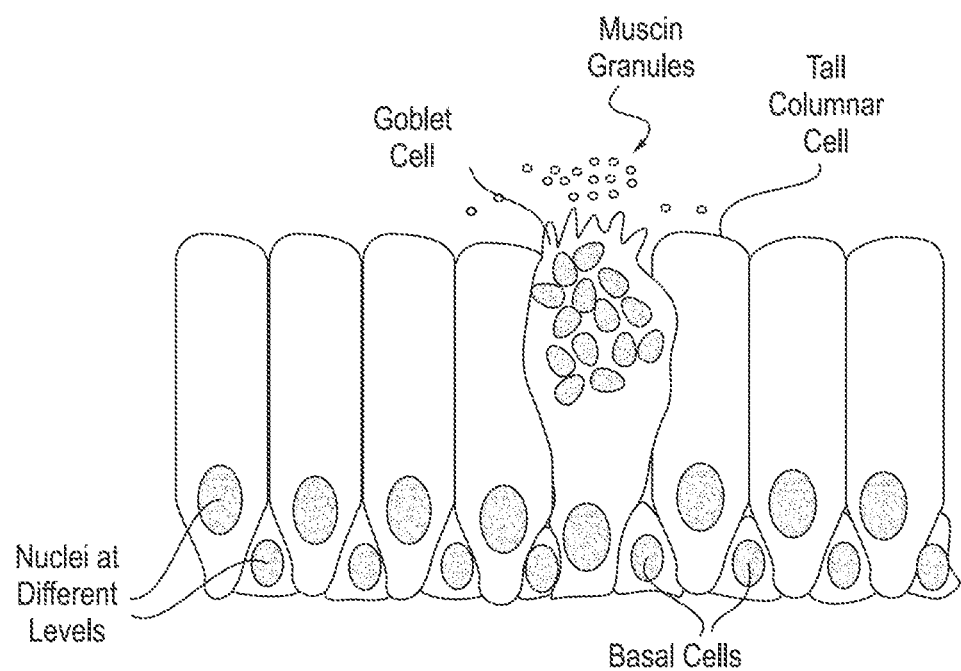
FIG. 1 is a side-view diagram of a mucus producing cell in the lining of a nasal epithelium.

FIGS. 1-5 are provided for background. FIG. 1 is a side-view diagram of a mucus producing cell in the lining of a nasal epithelium. Mucin granules tightly packed in the mucus producing cell (e.g. a goblet cell) before and after release. Before release, mucus condensation is achieved by the granules containing high concentrations of Ca2+, which acts as a "shielding" cation to nullify the repulsive forces within the molecule.

Figure 2:
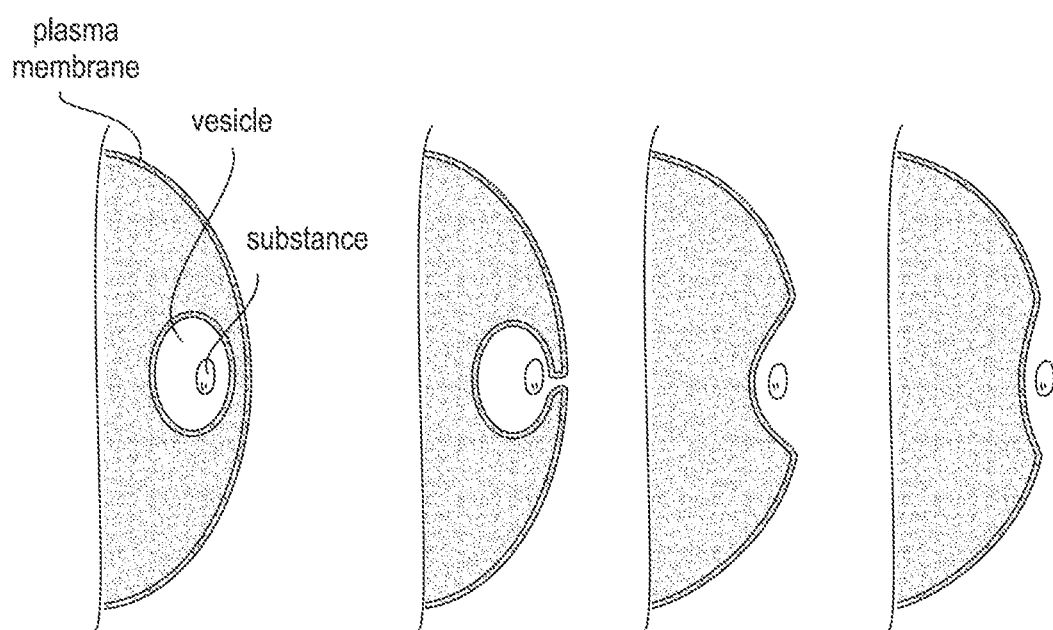
FIG. 2 is a diagram of a process of exocytosis.

FIG. 2 is a diagram of a process of exocytosis. As illustrated, an intracellular vesicle (membrane bounded sphere) containing mucins (substance) moves to the plasma membrane and subsequent fusion of the vesicular membrane and plasma membrane ensues.

Figure 3:
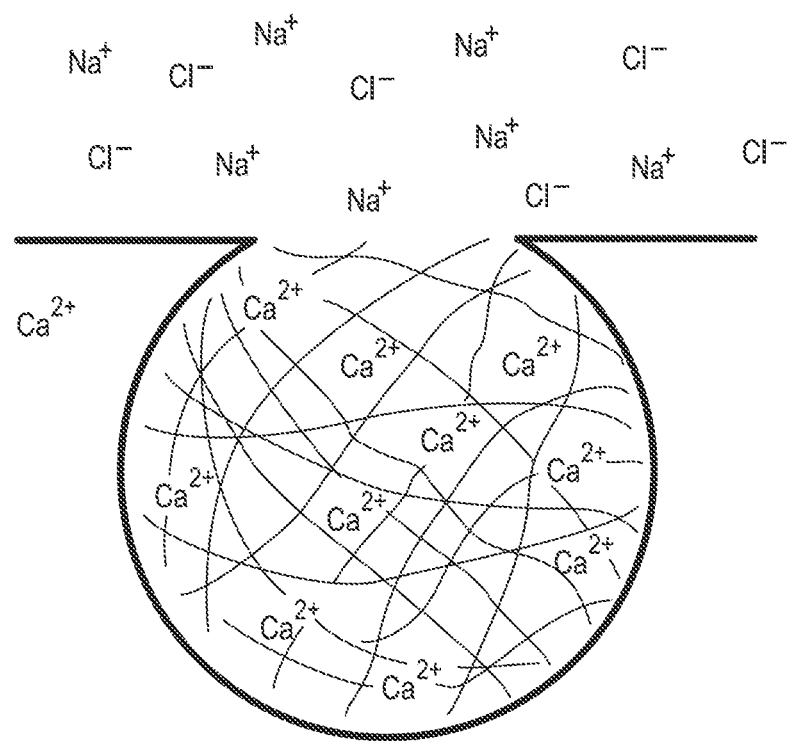
FIG. 3 is a diagram of a Ca2+ filled vesicle fusing with a membrane and opening up to an extracellular space containing Na+ and Cl−.

FIG. 3 is a diagram of a Ca2+ filled vesicle fusing with a membrane and opening up to an extracellular space containing Na+ and Cl−. The opening of the pore between intragranular space and extracellular space permits water, sodium (and other monovalent cations) to enter the vesicle and Ca2+ exit. Loss of charge-shielding allows electrostatic repulsion to rapidly expand the mucin polymer network, which facilitates hydration with the incoming water, and the resultant vastly expanded network erupts from the cell in the fashion of a "jack-in-the-box." The mucin expands from the vesicle into the extracellular space at a very rapid rate. This process of mucin granules in mucus producing cells escaping and forming mucus in the airway is known as exocytosis.

Figure 4A:
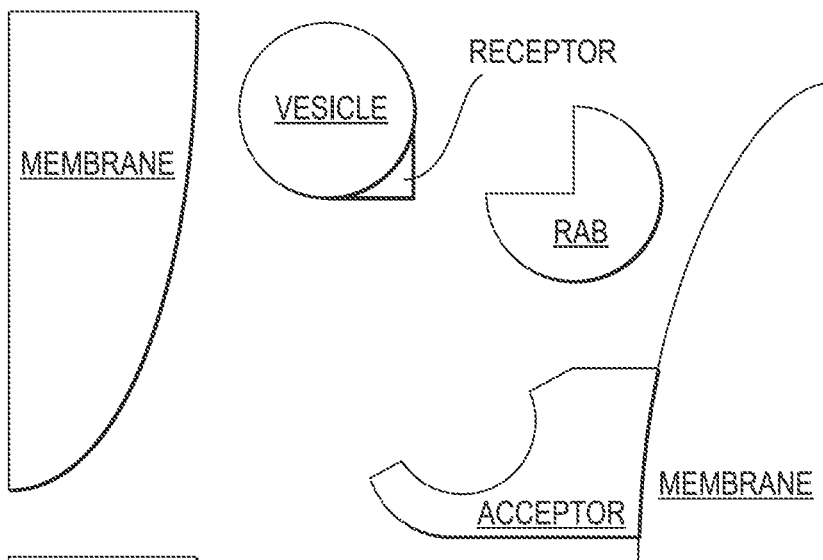
FIGS. 4A-4C are diagrams of a membrane-vesicle fusion process.
Figure 4B:
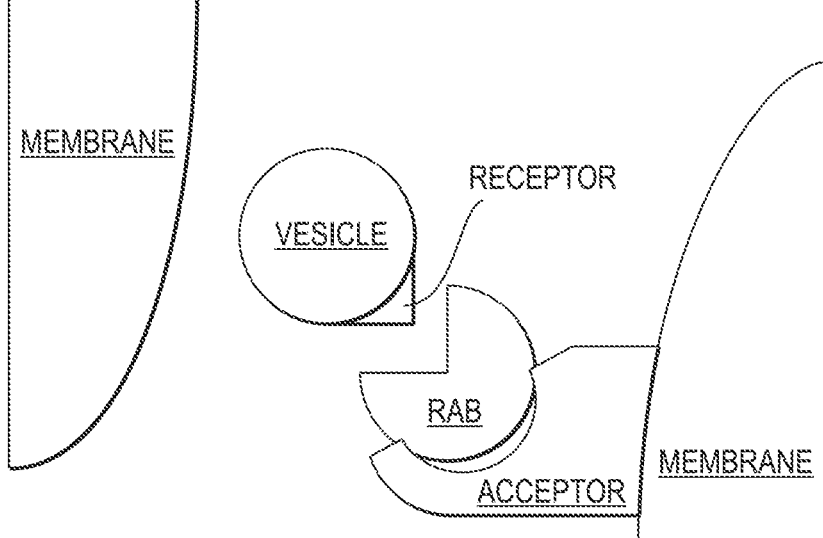
Figure 4C:
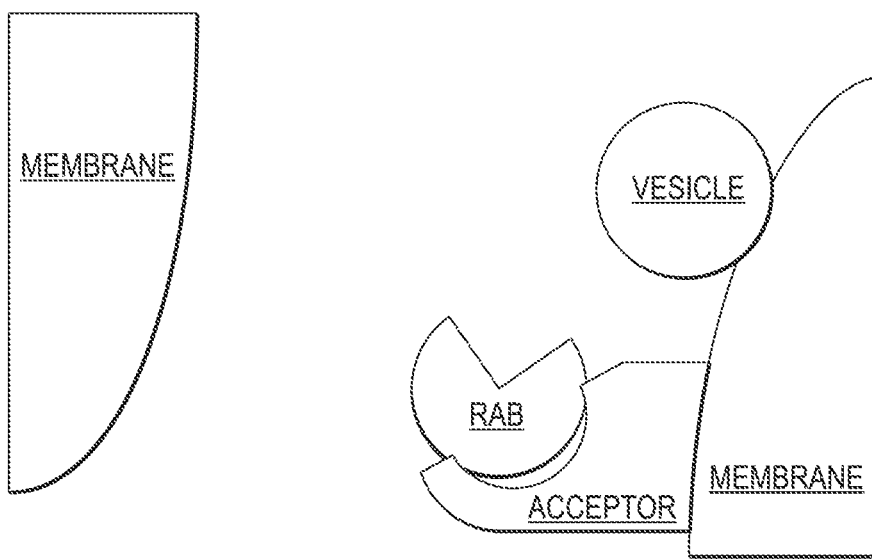

FIGS. 4A-C are diagrams of a membrane-vesicle fusion process. In FIG. 4A, the participants of the vesicle-membrane fusion are a vesicle with a receptor, a Rab protein, and a membrane with a receptor. The Rab family of proteins is a member of the Ras superfamily of monomeric G proteins. Only the active form of Rab GTPases is able to regulate membrane fusion.

In FIG. 4B, when the vesicle receptor is compatible with the Rab protein, the Rab protein docks onto the vesicle receptor and transports it towards the membrane acceptor. If the membrane acceptor is compatible with the Rab protein, docking occurs as shown.

In FIG. 4C, the Rab protein releases the vesicle to allow it to fuse with the membrane, thus kick-starting the exocytosis process illustrated in FIG. 3.

Figure 5:
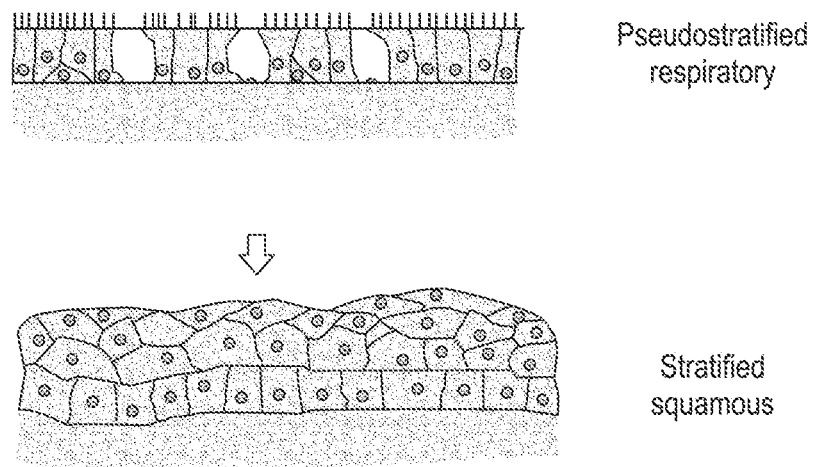
FIG. 5 is a side-view diagram of respiratory epithelium, illustrating a process of squamous metaplasia of columnar cells to squamous cells.

FIG. 5 is a side-view diagram of respiratory epithelium, illustrating a process of squamous metaplasia of columnar cells to squamous cells. The mucus producing cells are inactivated by undergoing cell metaplasia, the switching of cells from one type to another. In the presence of stimulants, the mucus producing cells, which are columnar cells, may switch to squamous cells to better protect themselves against these stimulants. When squamous metaplasia occurs, mucus is no longer produced due to the absence of mucus producing cells.

The measurement of secretion of mucins by mucus producing cells is made indirectly. Radiolabelled precursors of mucin are often used to quantify secretion in vitro and in vivo. Lectin staining, antibodies to mucus, staining with "mucus" stains (in particular Alcian blue and PAS), or usation of endogenous markers for mucus (for example fucose) may each be used to quantify the magnitude of mucus cell secretion. In some embodiments, it may be desirable to measure the secretion of mucins by mucus producing cells prior to, during and/or after a procedure.

PND occurs when mucus production is excessive and this excess mucus runs down the back of the throat, causing irritation. Modifying properties of the participants of the vesicle-membrane fusion and/or introducing stimulants to encourage squamous metaplasia decreases the likelihood of successful mucus production.

Some embodiments below provide apparatus and methods for reducing the amount of mucus production from each mucus-secreting cell by modifying the properties of the participants of the vesicle-membrane fusion. Other embodiments below provide apparatus and methods for deactivating mucus producing cells by impairing some or all of their mucus production and cell differentiation abilities, thus reducing the numbers of active mucus producing cells. Still other embodiments combine the two approaches of modifying and inactivating mucus producing cells.

In some embodiments, the amount of mucus production of each cell can be decreased by: a device or treatment limiting the number of mucins formed in the cell, a device or treatment modifying the mucin receptors such that the receptors are not highly compatible with Rab proteins, a device or treatment limiting the number of active form of Rab GTPases proteins available, and/or a device or treatment modifying the membrane acceptors such that the acceptors are not highly compatible with the Rab protein.

In some embodiments, the mucus producing cells can be deactivated by: a device or treatment destroying mucins in the cell, a device or treatment destroying mucin receptors such that they cannot receive Rab proteins, a device or treatment destroying the active form of Rab GTPases proteins, a device or treatment destroying membrane acceptors such that the acceptors cannot receive the Rab protein, and/or a device or treatment that causes metaplasia of the mucus producing cells into a non-mucus producing cell type.

In any one or more of the above mentioned embodiments, such modification and/or inactivation of mucus producing cells may include the application of energy by devices. In some embodiments, energy may be applied in the form of heat, radiofrequency (RF), laser, light, ultrasound (e.g. high intensity focused ultrasound), microwave energy, electromechanical, mechanical force, cooling, alternating or direct electrical current (DC current), chemical, electrochemical, cryogenic or others.

Any one or more of the above energy-application mechanisms may be used to re-shape, remodel, or change mechanical or physiologic properties of structures of a participant of the vesicle-membrane fusion. The modification results in a tightening, shrinking or enlarging of these participants, resulting in a change of shape, which impedes the exocytosis process.

In certain implementations, the energy-application mechanisms may be used to re-shape, remodel, or change the mechanical or physiologic properties of structures in order to cause mucus to divert. For example, one or more mucus paths may be diverted so mucus is moved to the lateral walls of the pharynx in addition to or instead of the posterior aspect of the pharynx. In certain implementations, diverting one or more mucus paths may be achieved by selectively treating certain areas of the upper airway.

In alternative embodiments, conformation changes (i.e., re-shaping) of participants of the vesicle-membrane fusion to impede the exocytosis process may include the healing process. For example, in some embodiments energy may be applied to a participant of the vesicle-membrane fusion in such a way that the healing process causes a change to the shape of the receptors, Rab, and acceptors.

In some embodiments, energy may be delivered into the cartilage tissue to cause a conformational change and/or a change in the physical properties of the cartilage. For example, in certain embodiments, the physical properties of the cartilage may be changed to divert or otherwise redirect the flow of mucus within the upper airway. Energy delivery may be accomplished by transferring the energy through the tissue covering the cartilage such as the epithelium, mucosa, sub-mucosa, muscle, ligaments, tendon and/or skin. In some embodiments, energy may also be delivered to the cartilage using needles, probes or microneedles that pass through the epithelium, mucosa, submucosa, muscle, ligaments, tendon and/or skin.

In some embodiments, energy may be delivered into the submucosal tissue to cause a conformational change and/or a change in the physical properties and/or type of the submucosal tissue. Energy delivery may be accomplished by transferring the energy through the tissue covering the submucosa such as the epithelium, mucosa, muscle, ligaments, cartilage, tendon and/or skin. In some embodiments, energy may also be delivered to the submucosa using needles, probes, microneedles, micro blades, or other non-round needles that pass through the epithelium, mucosa, muscle, ligaments, tendon and/or skin. In certain embodiments, the energy may be delivered through a combination of means. In certain embodiments, the energy may be delivered through one or both of surgical and non-surgical access.

In some embodiments, energy may be delivered to various tissues in order to achieve desired therapeutic results. The tissue may include, but is not limited to: cilia, goblet cells, nerves (such as the sphenopalatine ganglion), submucosal tissue, and other tissue. For example, in certain implementations, energy may be delivered to nerve tissue that controls the behavior of mucus producing cells or tissue.

Figure 6:
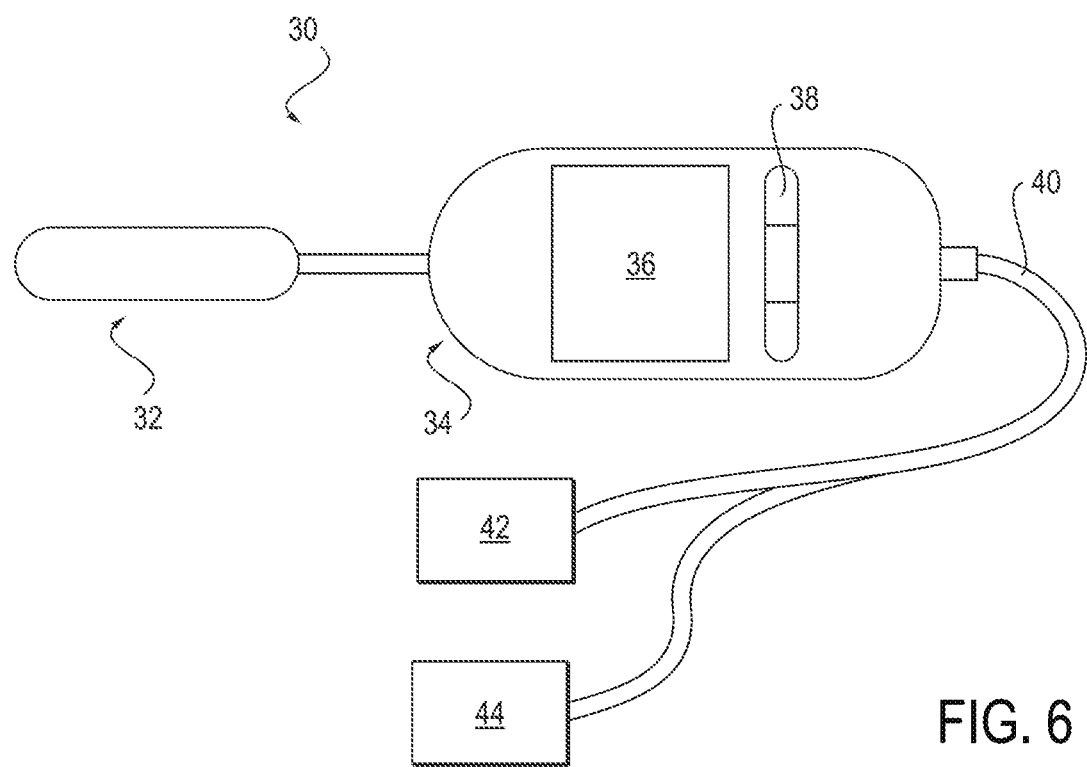
FIG. 6 is a top-view illustration of a mucus reduction treatment device, according to one embodiment.

FIG. 6 is a top-view schematic illustration of a mucus reduction treatment device 30, according to one embodiment. The device 30 comprises a treatment element 32 which may be configured to be placed inside the nasal cavity, nasal passage, nasal airway and/or throat to deliver the desired treatment. In some embodiments, the device 30 may further comprise a handle section 34 which may be sized and configured for easy handheld operation by a clinician. In some embodiments, a display 36 may be provided for displaying information to a clinician during treatment.

In some embodiments, the information provided on the display 36 may include treatment delivery information (e.g. quantitative information describing the energy being delivered to the treatment element) and/or feedback information from sensors within the device and/or within the treatment element. In some embodiments, the display may provide information on physician selected parameters of treatment, including time, power level, temperature, electric impedance, electric current, depth of treatment and/or other selectable parameters.

In some embodiments, the handle section 34 may also comprise input controls 38, such as buttons, knobs, dials, touchpad, joystick, etc. In some embodiments, controls may be incorporated into the display, such as by the use of a touch screen. In further embodiments, controls may be located on an auxiliary device which may be configured to communicate with the treatment device 30 via analog or digital signals sent over a cable 40 or wirelessly, such as via BLUETOOTH, WI-FI (or other 802.11 standard wireless protocol), infrared or any other wired or wireless communication method.

In some embodiments the treatment system may comprise an electronic control system 42 configured to control the timing, location, intensity and/or other properties and characteristics of energy or other treatment applied to targeted regions of a nasal passageway. In some embodiments, a control system 42 may be integrally incorporated into the handle section 34. Alternatively, the control system 42 may be located in an external device which may be configured to communicate with electronics within the handle section 34. A control system may include a closed-loop control system having any number of sensors, such as thermocouples, electric resistance or impedance sensors, ultrasound transducers, or any other sensors configured to detect treatment variables or other control parameters.

The treatment system may also comprise a power supply 44. In some embodiments, the power supply 44 may be integrally incorporated within the handle section 34. In alternative embodiments, the power supply 44 may be external to the handle section 34. An external power supply 44 may be configured to deliver power to the handle section 34 and/or the treatment element 32 by a cable or other suitable connection. In some embodiments, the power supply 44 may include a battery or other electrical energy storage or energy generation device. In other embodiments, the power supply 44 may be configured to draw electrical power from a standard wall outlet. In some embodiments, a power supply 44 may also include a system configured for driving a specific energy delivery technology in the treatment element 32. For example, the power supply 44 may be configured to deliver a radio frequency alternating current signal to an RF energy delivery element.

Alternatively, the power supply 44 may be configured to deliver a signal suitable for delivering ultrasound or microwave energy via suitable transducers. In further alternative embodiments, the power supply 44 may be configured to deliver a high-temperature or low-temperature fluid (e.g. air, water, steam, saline, or other gas or liquid) to the treatment element 32 by way of a fluid conduit.

In some embodiments, the treatment element 32 may have a substantially rigid or minimally elastic shape sized and shaped such that it substantially conforms to an ideal shape and size of a patient's nasal passageway and/or upper airway. In some embodiments, the treatment element 32 may have a curved shape, either concave or convex with respect to the interior of the lateral wall of the nasal passage and/or upper airway.

In some embodiments, the treatment element 32 may be configured to deliver energy (e.g. heat, RF, ultrasound, microwave) or cryo-therapy uniformly over an entire outer surface of the treatment element, thereby treating all nasal and/or upper airway tissues in contact with the treatment element 32. Alternatively, the treatment element 32 may be configured to deliver energy at only selective locations on the outer surface of the treatment element 32 in order to treat selected regions of upper airway tissues. In such embodiments, the treatment element 32 may be configured so that energy being delivered to selected regions of the treatment element 32 can be individually controlled. In some embodiments, portions of the treatment element 32 are inert and do not deliver energy to the tissue. In further alternative embodiments, the treatment element 32 may be configured with energy-delivery (or removal) elements distributed over an entire outer surface of the treatment element 32. The control system 42 may be configured to engage such distributed elements individually or in selected groups so as to treat only targeted areas of the upper airway passageway.

In some embodiments, the treatment element 32 may be configured to deliver heat energy to the upper airway tissues. In such embodiments, the treatment element 32 may comprise any suitable heating element available to the skilled artisan. For example, the treatment element 32 may comprise electrical resistance heating elements. In alternative embodiments, the heating element may comprise conduits for delivering high-temperature fluids (e.g. hot water or steam) onto the tissue. In some embodiments, a high-temperature fluid heating element may comprise flow channels which place high-temperature fluids into conductive contact with tissues (e.g. through a membrane wall) without injecting such fluids into the patient's nose. In further embodiments, any other suitable heating element may be provided. In further embodiments, the treatment element 32 may comprise elements for delivering energy in other forms such as light, laser, RF, microwave, cryogenic cooling, DC current and/or ultrasound in addition to or in place of heating elements. In alternative embodiments, similar effects can be achieved through the use of energy removal devices, such as cryogenic therapies configured to transfer heat energy out of selected tissues, thereby lowering the temperature of targeted tissues until a desired level of tissue modification is achieved.

In some embodiments, the treatment element 32 may be an inflatable balloon with energy delivery elements that deliver heat by circulating a fluid of elevated temperature though the inflated balloon during treatment. The balloon can also deliver cryotherapy (e.g. by circulating a low-temperature liquid such as liquid nitrogen) while it is enlarged to increase the surface area of contact between the treated tissue and treatment element 32.

Several embodiments may be employed for delivering energy treatment over a desired target area. For example, in some embodiments, a laser treatment system may treat a large surface area by scanning a desired treatment pattern over an area to be treated. In the case of microwave or ultrasound, suitably configured transducers may be positioned adjacent to a target area and desired transducer elements may be activated under suitable depth focus and power controls to treat a desired tissue depth and region. In some embodiments, ultrasound and/or microwave treatment devices may also make use of lenses or other beam shaping of focusing devices or controls. In some embodiments, one or more electrical resistance heating elements may be positioned adjacent to a target region, and activated at a desired power level for a therapeutically effective duration. In some embodiments, such heating elements may be operated in a cyclical fashion to repeatedly heat and cool a target tissue. In other embodiments, RF electrodes may be positioned adjacent to and in contact with a targeted tissue region. The RF electrodes may then be activated at some frequency and power level therapeutically effective duration. In some embodiments, the depth of treatment may be controlled by controlling a spacing between electrodes. In alternative embodiments, RF electrodes may include needles which may puncture a nasal or upper airway tissue to a desired depth (as shown for example in FIG. 10 and in other embodiments below).

In some embodiments, the treatment element 32 and control system 42 may be configured to deliver treatment energy or cryotherapy to a selected tissue depth in order to target treatment at specific tissues. For example, in some embodiments, treatments may be targeted at completely inactivating mucus producing cells. In other embodiments, treatments may be targeted at modifying the mucus production capacity of these cells.

In some embodiments, the treatment element 32 and control system 42 may be configured to deliver treatment energy to create specific localized tissue damage or ablation, stimulating the body's healing response to create desired conformational or structural changes that reduces the mucus producing ability of the mucus producing cells.

In some embodiments, the treatment element 32 and control system 42 may be configured to create specific localized tissue damage or ablation without the application of energy. For example the treatment element 32 may be configured to chemically cauterize tissue in an upper airway passage by delivering a cauterizing agent (e.g., silver nitrate, trichloroacetic acid, cantharidin, etc.) to the tissue. The treatment element 32 may comprise apertures configured to permit the cauterizing agent pass through to the upper airway. In some embodiment, the treatment element 32 may aerosolize the cauterizing agent. Other delivery methods are also contemplated. The treatment element 32 may comprise a lumen through which the cauterizing agent passes. The lumen may be fluidly connected to a reservoir or container holding the cauterizing agent. The device may comprise an input control (e.g., a button or switch) configured to control the delivery of the cauterizing agent. In some embodiments, the treatment element 32 comprises an applicator that can be coated in a cauterizing agent (e.g., dipped in a reservoir of cauterizing agent, swabbed with cauterizing agent, etc.) and the coated treatment element applicator may be applied to tissue to be treated. In some embodiments, the treatment element 32 may be configured to apply cauterizing agent to the patient over a prolonged period of time (e.g., 30 seconds, 1 minute, 2 minutes, etc.). In some embodiment, the treatment element 32 comprises shields configured to protect tissue surrounding the tissue to be treated from coming into contact with the cauterizing agent. In some embodiments, a separate element is used to shield tissue surrounding the tissue to be treated from coming into contact with the cauterizing agent. While such treatments may be performed without the application of energy, in some embodiments, they are performed in conjunction with energy treatments.

In some embodiments, the treatment device 30 is configured to position tissue to be treated. In some embodiments, the device 30 comprises features and mechanisms to pull, push or position the upper airway tissue into a placing such that it is accessible to the device 30. For example, suction, counter traction, or compression between two parts of the device 30 may be used.

In some embodiments, the treatment device 30 comprises one, two, three, four, or more molds configured to position tissue. The mold or positioning element may be fixed in size or may vary in size. The mold may also be fixed in shape or may vary in shape. For example, the size or shape of the element may be varied or adjusted to better conform to an upper airway passage of a patient. Adjustability may be accomplished using a variety of means, including, for example, mechanically moving the mold by way of joints, arms, guidewires, balloons, screws, stents, and scissoring arms, among other means. The mold may be adjusted manually or automatically.

In some embodiments, the treatment device 30 may be configured to heat specific tissue while maintaining a relatively lower temperature in other adjacent tissue. It may be beneficial to confine heat energy applied to mainly the tissue to be treated. Adjacent tissues such as a basement membrane and skin may be maintained at different temperatures. Limiting unwanted heating of non-target tissues may allow trauma and pain to be reduced, may reduce scarring, may preserve tissue function, and may also decrease healing time. Combinations of heat transfer and/or heat isolation may allow directed treatment of specific tissue such as cells, while excluding another tissue, such as skin, without surgical dissection.

In some embodiments, the mold or positioning element comprises a separate or integrated energy delivery or treatment element 32 (e.g., an electrode such as those described below with respect to FIGS. 12A-E). The treatment element 32 may be fixed or adjustable in size.

For example, the treatment element 32 may be adjusted to better conform to the upper airway passage of a patient. In the case of a separate positioning element and treatment element 32, a distance between the two elements may either be fixed or adjustable. Adjustability may be accomplished using a variety of means, including, for example, mechanically moving the mold by way of joints, arms, guidewires, balloons, screws, stents, and scissoring arms, among other means. In some embodiments, the mold or another part of the device 30 is configured to deliver cooling (discussed in more detail below). In some embodiments, the mold or repositioning element comprises a balloon configured to reposition and/or modify tissue. A balloon may also be configured to deliver energy such as heat using hot liquid or gas.

In some embodiments (e.g., as shown in FIG. 6) the treatment element 32 may comprise a substantially cylindrical central portion with a semi-spherical or semi-ellipsoid or another shaped end-cap section at proximal and/or distal ends of the treatment element 32. In alternative embodiments, the treatment element may comprise a substantially ellipsoid shape as shown, for example in FIGS. 7-10.

Figure 7:
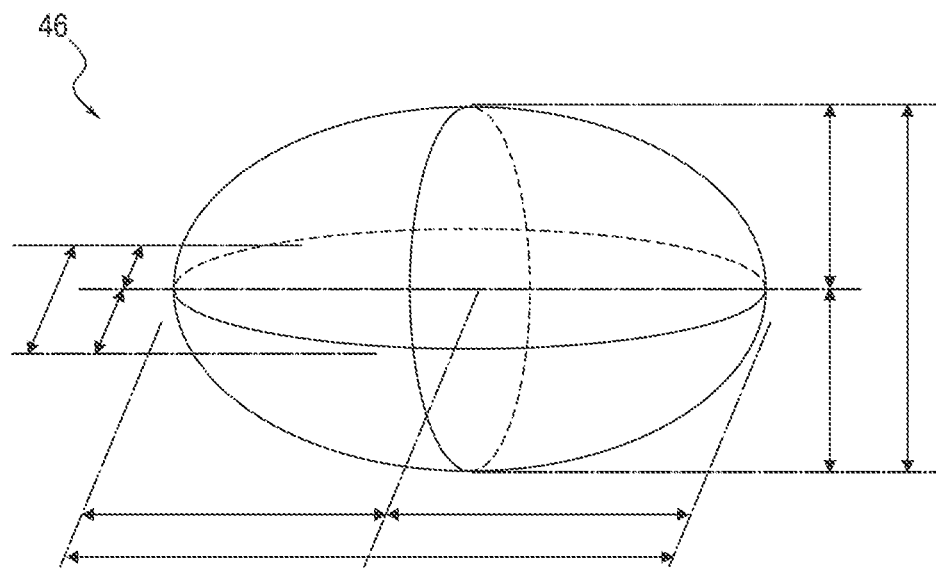
FIG. 7 is a perspective view of a treatment portion shape for a treatment portion of a mucus reduction treatment device, according to one embodiment.

FIG. 7 is a perspective diagram of a treatment portion shape for a treatment portion 46 of a mucus reduction treatment device, according to one embodiment. In some embodiments, the treatment portion 46 may be an ellipsoid balloon having an asymmetrical shape. In alternative embodiments, the treatment portion 46 may have an asymmetrical "egg-shape" with a large-diameter proximal end and a smaller diameter distal end. Any suitable solid or expandable medical balloon material and construction available to the skilled artisan may be used.

Figure 8:
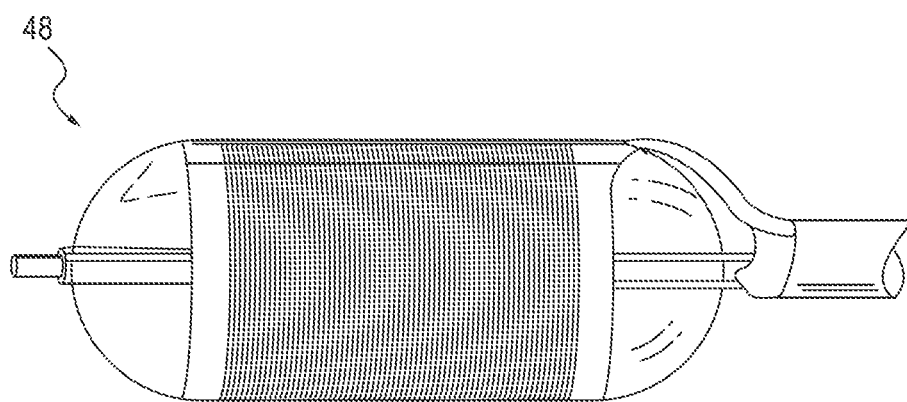
FIG. 8 is a perspective view of a treatment portion of a mucus reduction treatment device, according to an alternative embodiment.

FIG. 8 is a perspective illustration of a treatment portion 48 of a mucus reduction treatment device, according to an alternative embodiment. The treatment portion 48 may be configured to deliver energy to an interior of an upper airway. In some embodiments, the treatment element 48 may include an expandable balloon.

Figure 9A:
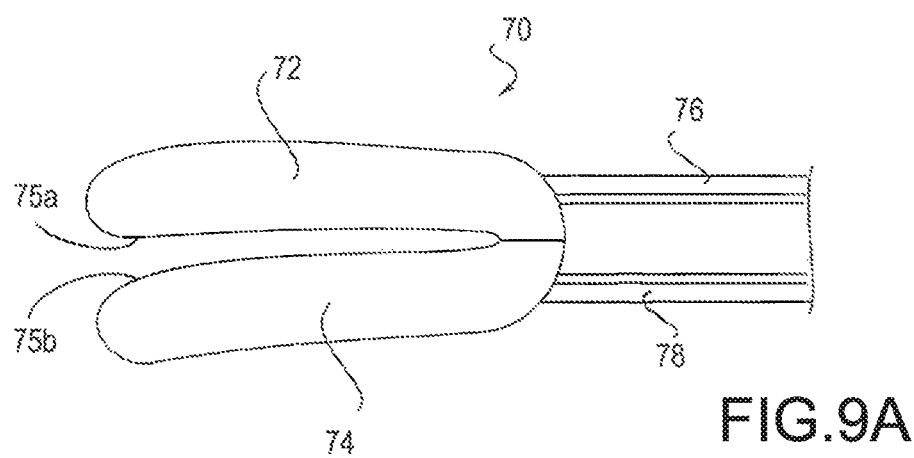
FIG. 9A is a perspective view of a treatment portion of a mucus reduction treatment device, according to another alternative embodiment.
Figure 9B:
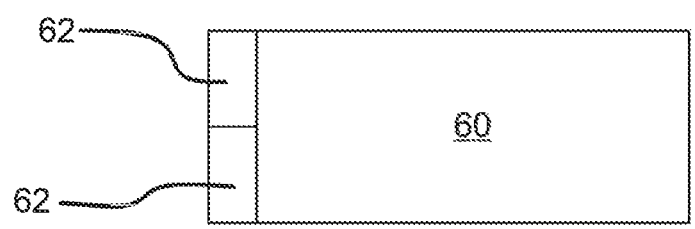
FIG. 9B is a perspective view of an expandable treatment element of a mucus reduction treatment device, according to another alternative embodiment.

FIG. 9A is a perspective illustration of a bifurcated treatment element 70 of a mucus reduction treatment device, according to another alternative embodiment. The bifurcated treatment element 70 may have a pair of semi-ellipsoid elements 72, 74 sized and configured to be inserted into the nose with one element 72, 74 on either side of the septum. The elements may each have a medial surface 75a and 75b, which may be substantially flat, curved or otherwise shaped and configured to lie adjacent to (and possibly in contact with) the nasal septum. In some embodiments, the elements 72, 74 may include expandable balloons with independent inflation lumens 76, 78. In alternative embodiments, the elements 72, 74 have substantially fixed non-expandable shapes. In still further embodiments, the elements 72, 74 may include substantially self-expandable sections. In some embodiments, the bifurcated treatment element halves 72, 74 may also carry energy delivery structures as described elsewhere herein. In some embodiments, the shape of the elements 72, 74 may be modified by the operator to impart an optimal configuration to the treated tissue.

Some embodiments of treatment elements may comprise one or more inflatable or expandable sections configured to expand from a collapsed configuration for insertion into the nasal passageway and/or throat, to an expanded configuration in which some portion of the treatment element contacts and engages an internal surface of an upper airway. In some embodiments, an expandable treatment element may comprise an inflation lumen configured to facilitate injection of an inflation medium into an expandable portion of the treatment element. In alternative embodiments, an expandable treatment element 60 (FIG. 9B) may comprise one or more segments 62 comprising a shape-memory alloy material which may be configured to expand to a desired size and shape in response to a change of temperature past a transition temperature. In some embodiments, such a temperature change may be brought about by activating an energy-delivery (or removal) element in the treatment element 60.

In some embodiments, the treatment element 60 may expand with various locations on the element 60 expanding to different configurations or not expanding at all to achieve a desired shape of the treatment element 60. In some embodiments, such expandable treatment elements 60 or segments 62 may be elastic, inelastic, or pre-shaped. In some embodiments, expandable treatment elements 60 or segments 62 thereof may be made from shape-memory metals such as nickel-cobalt or nickel-titanium, shape memory polymers, biodegradable polymers or other metals or polymers. Expandable balloon elements may be made of any elastic or inelastic expandable balloon material.

Figure 10:
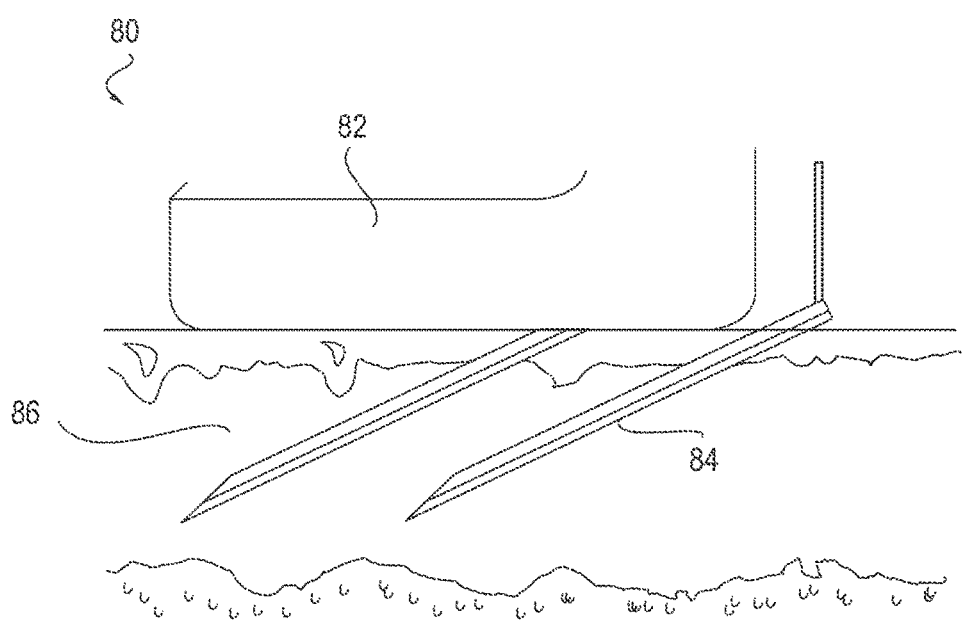
FIG. 10 is a cross-sectional view of a distal end of a treatment portion of a treatment device, showing microneedles puncturing tissue in order to apply treatment at a desired tissue depth, according to one embodiment.

FIG. 10 is a cross-sectional view of a distal end 80 of a treatment portion 82 of a treatment device, showing microneedles 84 puncturing tissue 86 in order to apply treatment at a desired tissue depth, according to one embodiment.

Treatment elements may be generally configured to be used once and removed from a patient's upper airway once a treatment is delivered. In some embodiments, treatments may further involve placing longer term treatment elements, such as stents, molds, external strips, etc. for a period of time after treatment.

Figure 11:
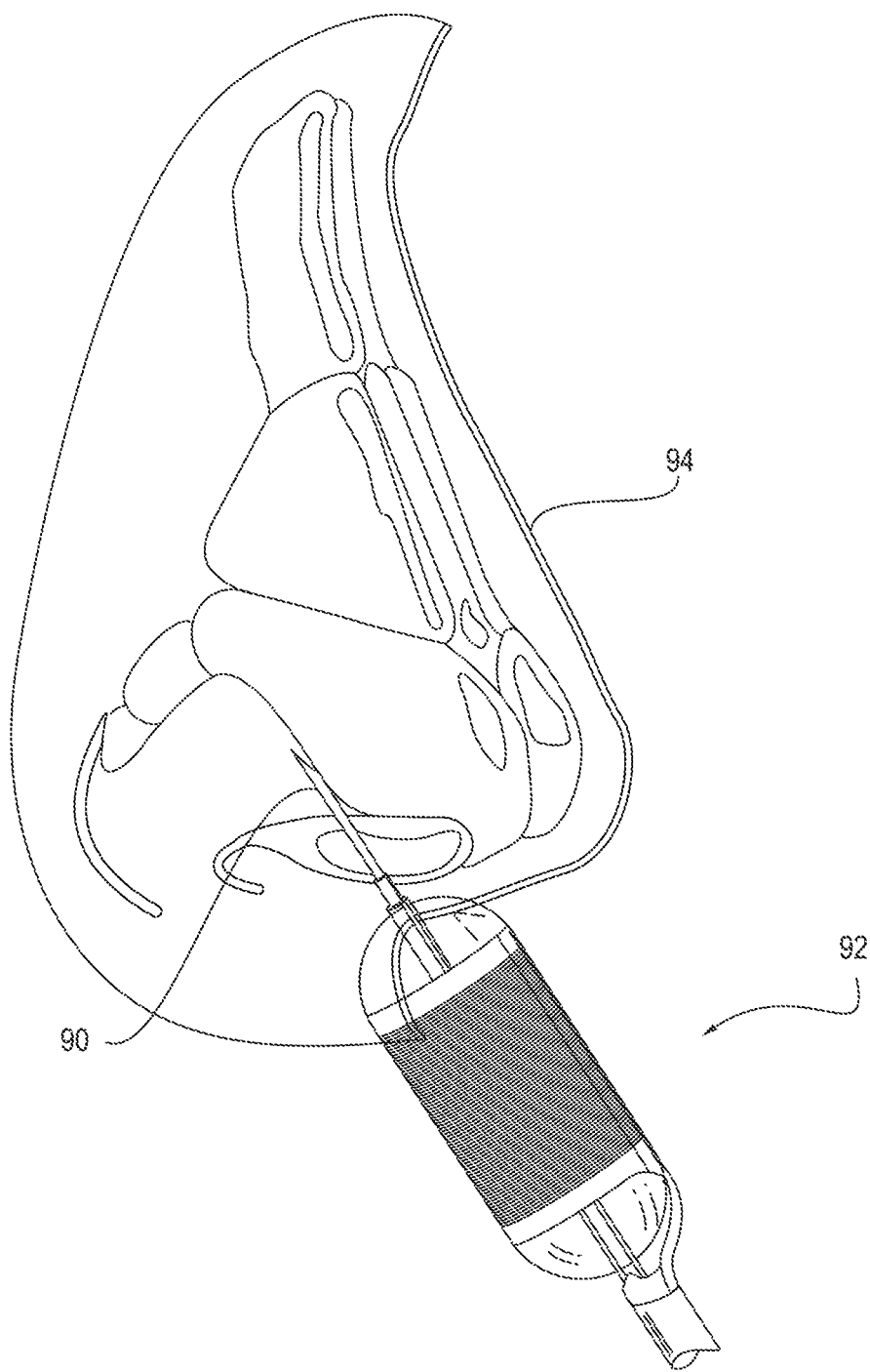
FIG. 11 is a perspective view of an energy delivery balloon being inserted into a nose, according to one embodiment.

FIG. 11 is a perspective view of an energy delivery balloon 92, including a needle portion 94 being inserted into a nose 90, according to one embodiment.

Examples of Various Electrode Arrangements

Described below are embodiments of various treatment devices and, more particularly, electrode arrangements that may be used for applying energy to the upper airway. These electrodes may, for example, deliver RF energy to modify properties of mucus producing cells and/or glands to reduce mucus production. In some embodiments, one or more electrodes may be used alone or in combination with a tissue positioning device or mold.

In other embodiments, one or more electrodes may be integrally formed with a tissue positioning device or mold, so that the electrodes themselves hold the position of the tissue. In some embodiments, the energy delivery devices may use alternating current. In some embodiments, the energy delivery devices may use direct current. In certain such embodiments, the energy delivery device may comprise a configuration using a grounding pad.

In some embodiments, the term "electrode" refers to any conductive or semi-conductive element that may be used to treat the tissue. This includes, but is not limited to metallic plates, needles, and various intermediate shapes such as dimpled plates, rods, domed plates, blades, etc. Electrodes may also be configured to provide tissue deformation in addition to energy delivery. Unless specified otherwise, electrodes described can be monopolar (e.g., used in conjunction with a grounding pad) or bipolar (e.g., alternate polarities within the electrode body, used in conjunction with other tissue-applied electrodes). In some embodiments, "counter-traction" refers to applying a force opposite the electrode's primary force on the tissue to increase stability, adjustability, or for positioning tissue.

Figure 12A:
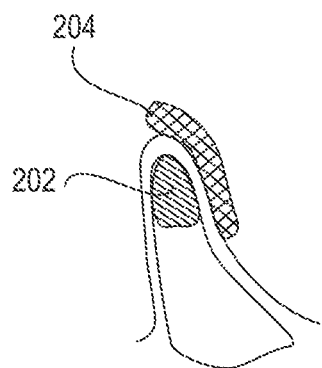
FIGS. 12A-12E are cross-sectional views of various electrode arrangements for applying energy to the treatment tissue in the nose or throat according to various embodiments.

FIGS. 12A-E are cross-sectional views of various electrode arrangements for applying energy to the treatment tissue in the nose or throat according to various embodiments. As shown in FIG. 12A, in some embodiments, bipolar electrodes may be used to deliver energy, with one electrode 202 placed internally in the nose or throat, and one electrode 204 placed externally on the outside of the nose or throat. This embodiment may advantageously provide direct current flow through the tissue with no physical trauma from needles (as shown in some embodiments below).

Figure 12C:
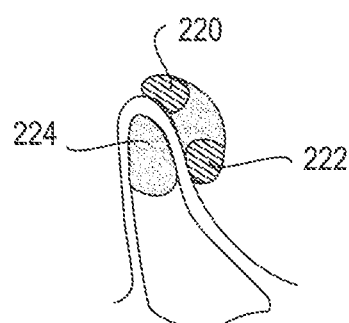
Figure 12B:
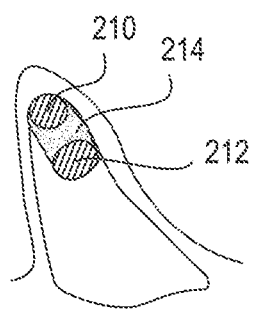

As shown in FIG. 12B, in some embodiments, bipolar electrodes may be used to deliver energy, with both electrodes 210, 212 placed internally. An insulating spacer 214 may be placed between them. This embodiment may be simple and may advantageously minimize current flow through the skin layer.

FIG. 12C illustrates certain embodiments wherein bipolar electrodes 220, 222 may be both placed externally and may be connected to a passive positioning element 224 placed inside the nose or throat, adjacent to tissue to be treated. This embodiment may advantageously minimize the potential for mucosal damage. In some embodiments, electrodes placed internally may be shaped to function as a positioning element or may comprise an additional structure that may function as a positioning element.

Figure 12D:
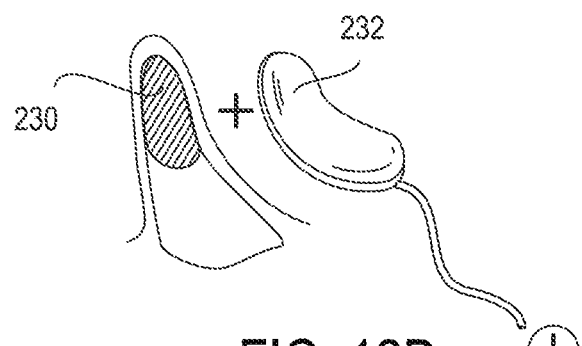

FIG. 12D illustrates certain embodiments wherein a monopolar electrode 230 may be used to deliver energy. The electrode 230 may be placed internally and may be connected to an external, remote grounding pad 232. The grounding pad 232 may, for example, be placed on the abdomen of a patient or in other desired locations. This embodiment may advantageously be simple to manufacture and may minimize current flow through the skin. In some embodiments, a monopolar electrode may be placed externally and may be connected to a positioning element placed inside the nose or throat as well as a remote grounding pad. This embodiment may also advantageously be simple to manufacture, may minimize mucosal current flow, and may also be simple to position. In some embodiments, electrodes placed internally may be shaped to function as a positioning element or may comprise an additional structure that may function as a positioning element.

Figure 12E:
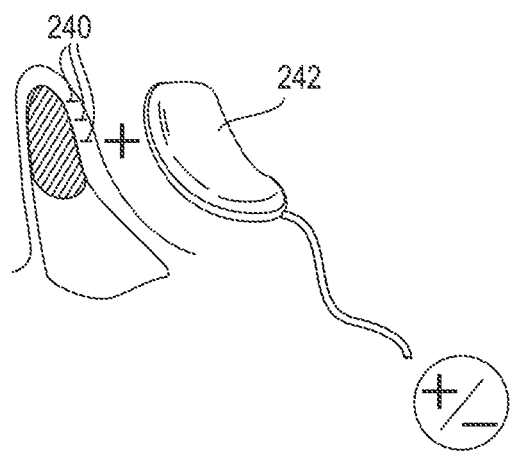

FIG. 12E illustrates certain embodiments wherein monopolar transmucosal needle electrodes 240 may be used to deliver energy. The needle electrodes 240 may be placed internally and penetrate through the mucosa to the cartilage. A remote grounding pad 242 or element may be placed externally. In some embodiments, monopolar transmucosal needles may be used in conjunction with one or more positioning elements which may be disposed on or around the needles. In some embodiments, monopolar transdermal needles may be used to deliver energy. In other embodiments (not shown), the needles may be placed external to the nose or throat, and penetrate through to tissue to be treated. Needle configurations may advantageously target the upper airway tissue to be treated specifically. The monopolar transdermal needles may be used in conjunction with an internal positioning device (not shown).

In some embodiments, bipolar transmucosal needles may be used to deliver energy to tissue to be treated. The needles may be placed internally, with an insulating spacer between them and may penetrate through cell membrane to the mucins and/or Rab and/or other exocytosis components to be treated. In some embodiments, the bipolar transmucosal needles may be used in combination with one or more internal positioning elements. The one or more positioning elements may be placed on or near the needles. In some embodiments, bipolar transdermal needles may be used to deliver energy. In other embodiments, the transdermal needles may be placed externally and penetrate through to tissue to be treated. Needle configurations may advantageously target the mucus producing cells to be treated specifically. The transdermal bipolar needles may be used in conjunction with an internal positioning element.

Figure 13:
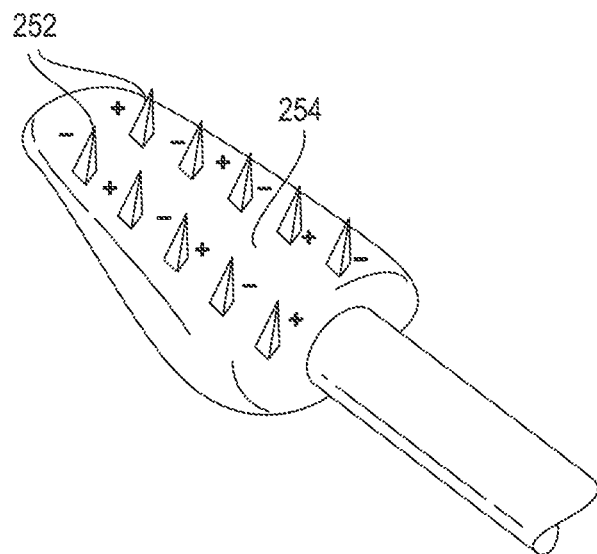
FIG. 13 is a perspective view of an electrode arrangement of a treatment element according to one embodiment.

FIG. 13 is a perspective view of an electrode arrangement of a treatment element 250 according to one embodiment. An array of electrodes comprising one, two, or many pairs of bipolar needles 252 may be located on the treatment element 250 and be configured to be placed into contact with the mucus producing cells. An insulator 254 may be disposed between the bipolar needles 252. An insulator may also be used on part of the needle's length to allow energy to be delivered only to certain tissue structures, such as mucus producing cells. The electrodes may be placed either internally or transmucosally or they may be placed externally or transdermally. In some embodiments, the insulator 254 may also function as a positioning element. In other embodiments (not shown), the array of electrodes may be used in conjunction with a separate tissue positioning element.

Figure 14:
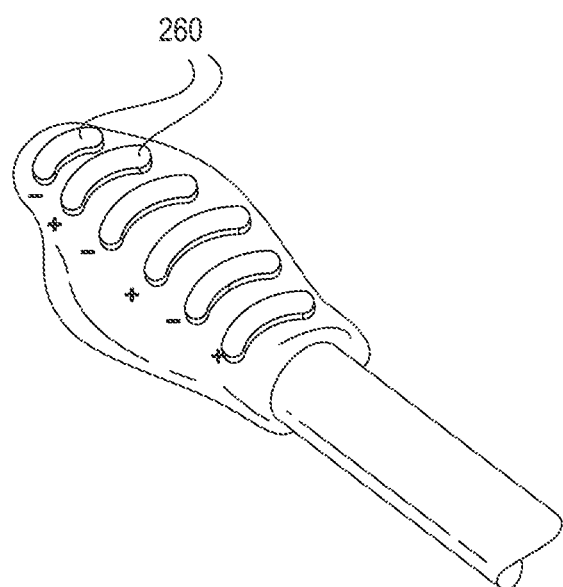
FIG. 14 is a perspective view of an electrode arrangement of a treatment element according to one embodiment.

FIG. 14 is a perspective view of an electrode arrangement of a treatment element 256 according to one embodiment. The treatment element 256 may comprise one, two or many pairs of bipolar electrodes 258. An insulator 260 may be disposed between the bipolar electrodes 260. As opposed to the electrode arrangement shown in FIG. 13, where the pairs of electrodes are arranged side-by-side, the embodiment of FIG. 14 arranges the pairs of electrodes 258 along the length of the treatment element 256. In some embodiments, the electrodes may be non-penetrating, in contrast to the needles 252 of FIG. 13. The electrodes 258 may be placed against either the skin, externally, or the mucosa, internally as a means of delivering energy to target tissue such as mucus producing cells.

In some embodiments of treatment devices comprising an array or multiple pairs of electrodes, each pair of electrodes (bipolar) or each electrode (monopolar) may have a separate, controlled electrical channel to allow for different regions of the treatment element to be activated separately. For example, in some embodiments, needles or needle pairs may be individually controlled to produce an optimal treatment effect. For another example, in some embodiments, separate electrodes (e.g. those of FIGS. 12B and 12C) may be individually controlled to produce an optimal treatment effect. Other examples are also contemplated. The channels may also comprise separate or integrated feedback. This may advantageously allow for more accurate temperature control and more precise targeting of tissue. Separate control may also allow energy to be focused and/or intensified on a desired region of the treatment element in cases where the anatomy of the upper airway tissue/structures does not allow the entire electrode region of the treatment element to engage the tissue. In such embodiments, the upper airway tissue that is in contact with the treatment element may receive sufficient energy to treat the tissue.

Figure 15A:
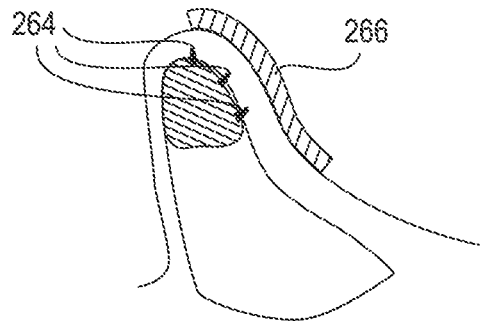
FIGS. 15A-15C are cross-sectional views of various electrode arrangements for applying energy to the treatment tissue in the nose or throat according to various embodiments.
Figure 15B:
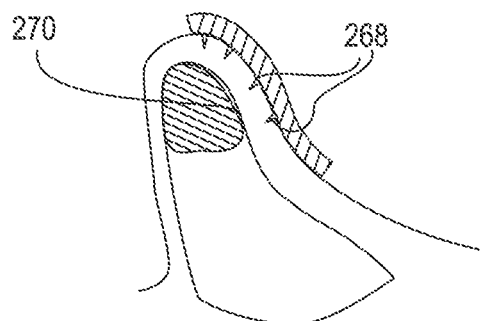
Figure 15C:
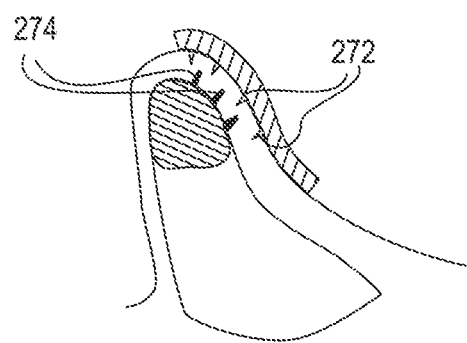

FIGS. 15A-C are cross-sectional views of various electrode arrangements for applying energy to the treatment tissue in the nose or throat according to various embodiments. Combinations of the described electrode configurations may be used to deliver energy to tissue to be treated. For example, FIG. 15A illustrates internally-placed transmucosal needles 264 penetrating through to tissue to be treated and an external electrode 266 according to one embodiment. This embodiment may advantageously target the mucus producing and/or controlling cells specifically and be biased for mucosal preservation.

FIG. 15B illustrates externally-placed transdermal needles 268 and an internally-placed electrode 270 according to one embodiment. This embodiment may advantageously target the mucus producing and/or controlling cells specifically and be biased towards skin preservation.

FIG. 15C illustrates bipolar needle electrodes 272, 274 be placed both transdermally or externally and transmucosally or internally according to one embodiment. This embodiment may advantageously target the mucus producing cells specifically. Some embodiments of treatment elements may include inert areas which do not delivery energy to the tissue. Other combinations of electrode configuration are also possible.

Multi-Channel Configuration

During treatment, each pair of electrodes may have varying degrees of contact with the tissue, depending on the skills and habits of the device user. For a configuration in which all pairs of electrodes are controlled by one main electrical channel, this can lead to varying magnitudes of treatment energy passing through each electrode pair.

The pair/pairs of electrode that has/have a higher degree of contact with the tissue, will experience higher magnitudes of impedance in their/its individual circuit. Since treatment energy takes the path of least resistance, this can lead to treatment energy being diverted to the other pair/pairs of electrodes that experiences/experience a relatively lower magnitude of impedance due to relatively lower degrees of tissue contact.

This creates a situation in which the treatment energy flowing through each pair of electrodes is not repeatable due to the electrodes-tissue contact being user dependent. To ensure a greater degree of control and accuracy over the treatment energy through each electrode, each pair of electrodes may have a separate, controlled electrical channel to allow for different regions of the treatment element to be activated separately. Each electrode pair may also be paired up with its own thermocouple.

An intermittent electrode-tissue contact may also result in coagulum forming due to fluctuating waveform. When electrode-tissue contact is intermittent, the impedance value fluctuates and the power delivered also has to adapt rapidly in order to reach or maintain set temperature. This may be conducive for coagulum to form on the electrode, causing impedance to rise. This starts a cycle of escalating power delivered and impedance increment with coagulum build up on the electrodes, causing the treatment process to be less effective. Hence, there is a need for a system set up which ensures repeatable and controllable delivery of treatment energy to each electrode pair in order to achieve the desired surgery outcome. The system may comprise one or more thermocouples and an RF output channel assigned to each electrode pair for feedback.

Figure 16A:
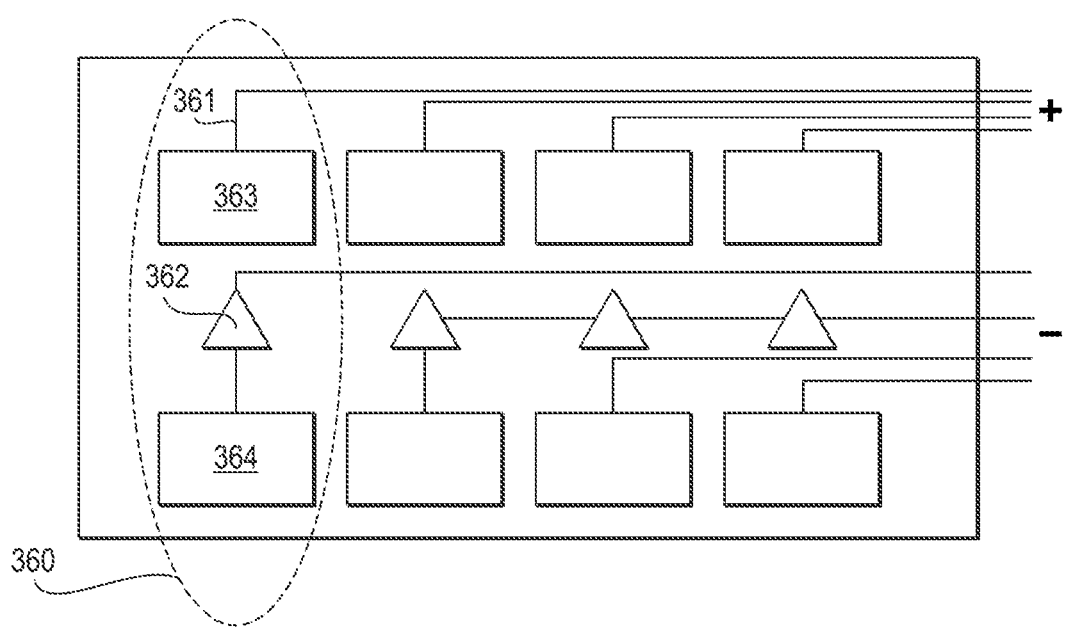
FIGS. 16A-16I are cross-sectional views of various permutations of electrodes-thermocouples combinations for a multi-channel configuration according to various embodiments.

FIGS. 16A-I are cross-sectional views of various permutations of electrodes-thermocouples combinations for a multi-channel configuration according to various embodiments. FIG. 16A illustrates a cross-sectional view of an electrode arrangement according to one embodiment, including a row of positive electrodes spaced from a row of negative electrodes and a row of thermocouples, including electrode 363 and electrode 364. A pair of electrodes 363, 364 may have its own individual subsystem 360 of controlled RF output channel 361 and thermocouple 362 to allow for independent adjustments. The thermocouple 362 act as a feedback-control to ensure that proper temperature is maintained at the site of surgery.

In certain implementations, the nasal treatment device may include one or more thermocouples 362 and an RF output channel 361 assigned to each electrode pair for feedback. An electrode pair may include a positive electrode 363 and a negative electrode 364. In some embodiments, the positive electrode 363 and the negative electrode 364 may be positioned opposite to one another. Each electrode pair may have its own individual subsystem 360. The individual subsystem 360 may include a controlled RF output channel 361 and a thermocouple 362 to allow for independent adjustments. The thermocouple 362 may act as a feedback control to ensure that proper temperature is maintained at the site of treatment.

Figure 16B:
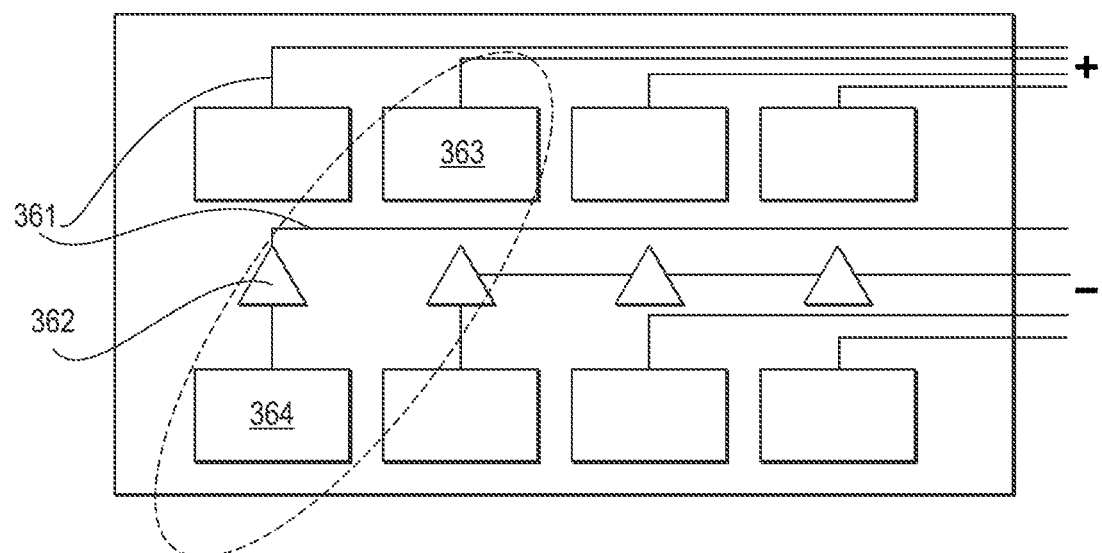

FIG. 16B illustrates a cross-sectional view of an electrode arrangement according to one embodiment that provides a means to allow pairing of any of the positive electrode to any of the negative electrode to form a complete circuit. A positive electrode 363 may be paired with the opposite negative electrode (e.g., as shown in FIG. 16A) or to any of the other negative electrodes (e.g. negative electrode 364) regardless of its location in the device. The device may include a plurality of thermocouples 362 and an RF output channel 361 assigned to each pair of electrodes for feedback. Temperature readings from two adjacent thermocouples 362 may be averaged to obtain a temperature reading for the region in which the circuit is located. In some embodiments, the two thermocouples 362 may be the thermocouples in the closest proximity to the positive electrode 363 and the negative electrode 364.

Figure 16C:
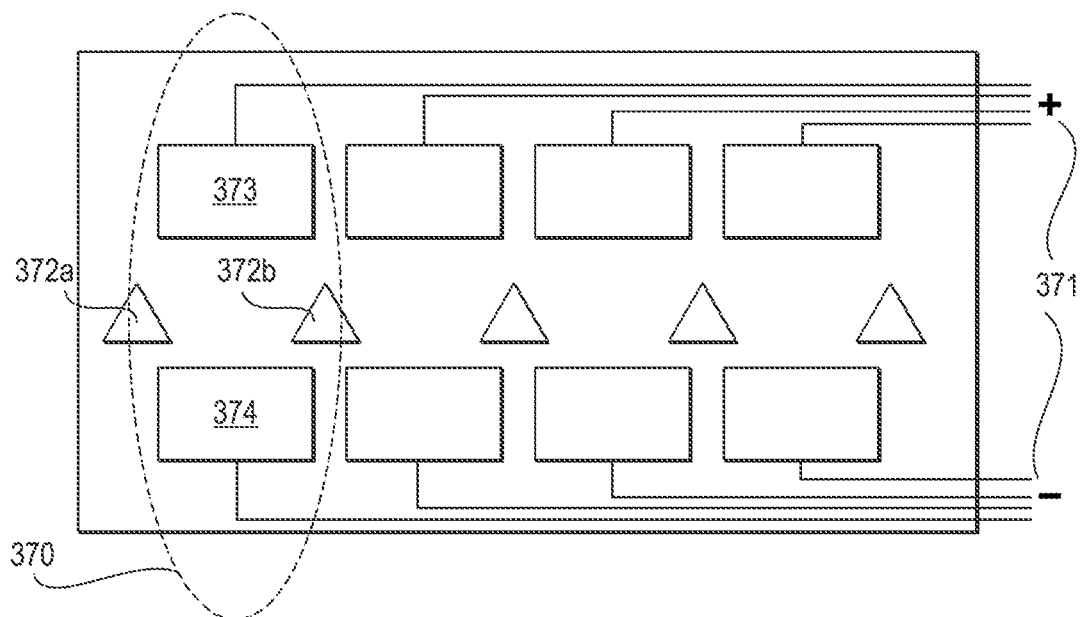

FIG. 16C illustrates a cross-sectional view of an electrode arrangement according to one embodiment. In certain embodiments, the electrode array may be arranged such that each electrode pair of the array of electrodes may have its own individual subsystem 370. An electrode pair may include a positive electrode 373 and a negative electrode 374. Each individual subsystem 370 may include controlled RF channels 371, a first thermocouple 372a, and a second thermocouple 372b to allow for independent temperature readings and/or individual temperature adjustments. In certain implementations, the temperature input signals sensed from neighboring thermocouples 372a and 372b are electronically subtracted from each other and act as a feedback-control to ensure that proper temperature is maintained at the treatment site. In certain implementations, a temperature reading for an individual subsystem 370 may be obtained from the average temperature input signals of the neighboring thermocouples 372a and 372b. The temperature reading may act as a feedback control to ensure that proper temperature is maintained at the treatment site.

Figure 16D:
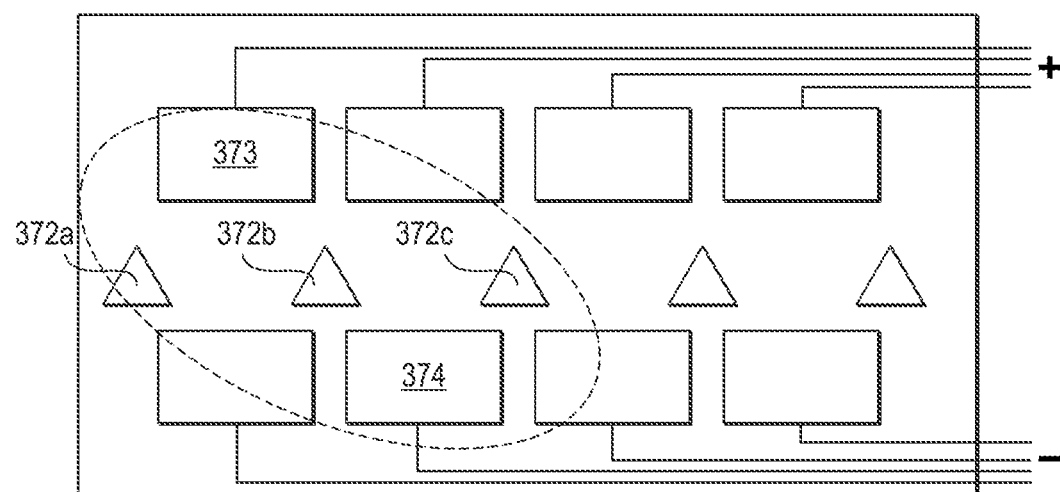
Figure 16E:
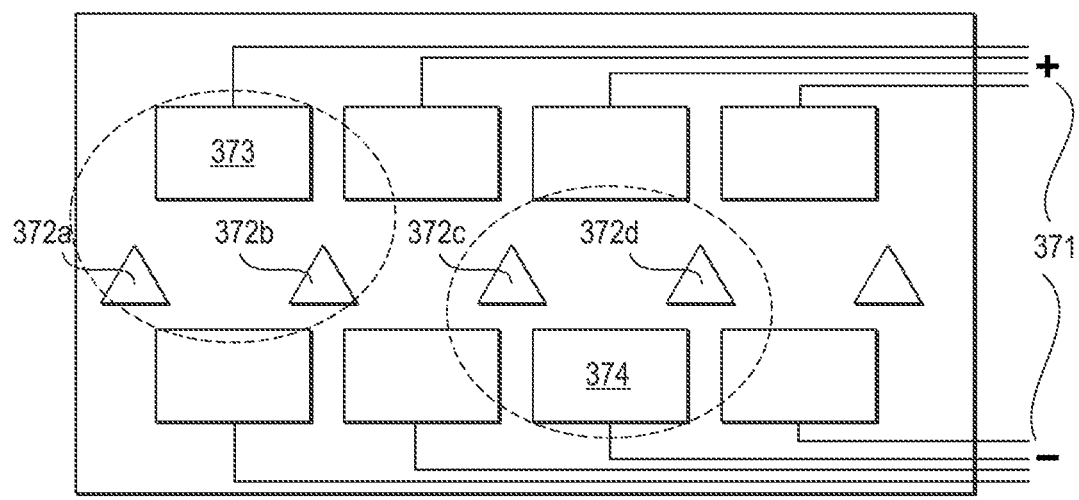

FIGS. 16D and 16E illustrate a cross-sectional view of an electrode arrangement according to various embodiments. In certain implementations, a device may include multiplexed configurations by providing functionality to allow pairing of any of the positive electrodes 373 to any of the negative electrodes 374 to form a complete circuit. A positive electrode 373 may be paired with the opposite negative electrode 374, or to any of the other negative electrodes 374 regardless of its location in the device. FIG. 16D shows one example where temperature readings may be the average of three adjacent thermocouples 372a, 372b, and 372c. FIG. 16E shows one example where temperature reading may be the average of four adjacent thermocouples 372a, 372b, 372c, and 372d. It will be appreciated that the average of any number of thermocouples may be used to obtain a temperature reading.

Figure 16F:
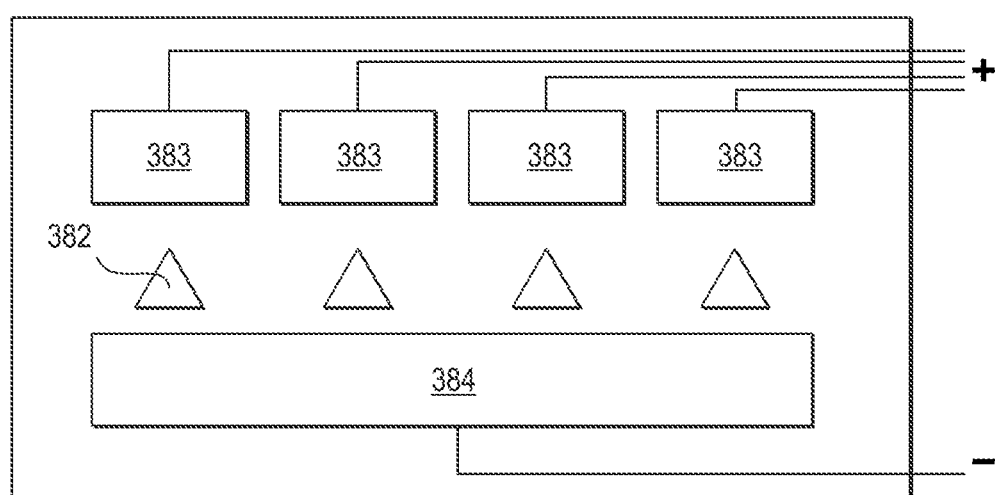

FIG. 16F illustrates a cross-sectional view of an electrode arrangement according to one embodiment. In certain implementations, the positive electrodes 383 may be configured to share a common negative electrode 384. While the negative electrode 384 is common, each positive electrode 383 may be independently controlled to achieve desired treatment. In some embodiments, a temperature reading may be obtained from temperature input signals sensed from one or more thermocouple 382. In certain implementations, each RF output channel may comprise a positive electrode and the negative electrode.

Figure 16G:
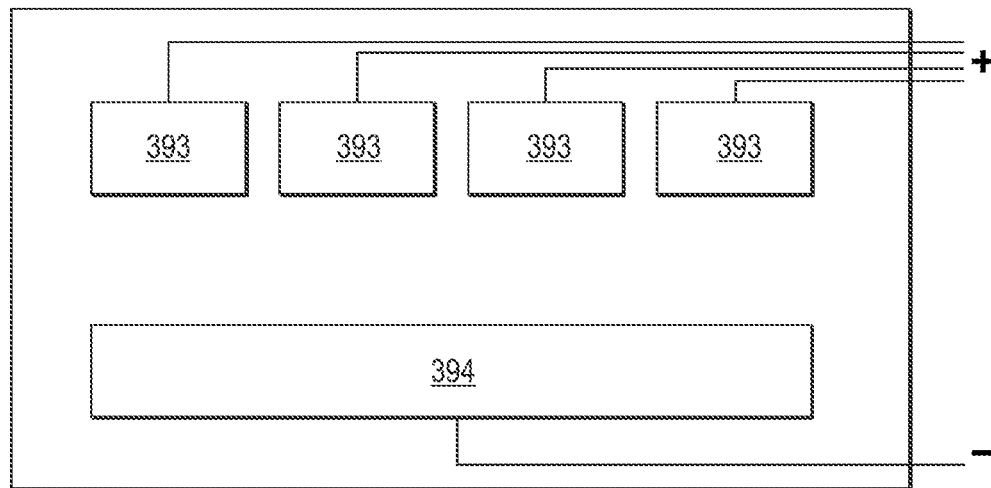

FIG. 16G illustrates a cross-sectional view of an electrode arrangement according to one embodiment. In certain implementations, all the positive electrodes 393 may share a common negative electrode 394.

Figure 16H:
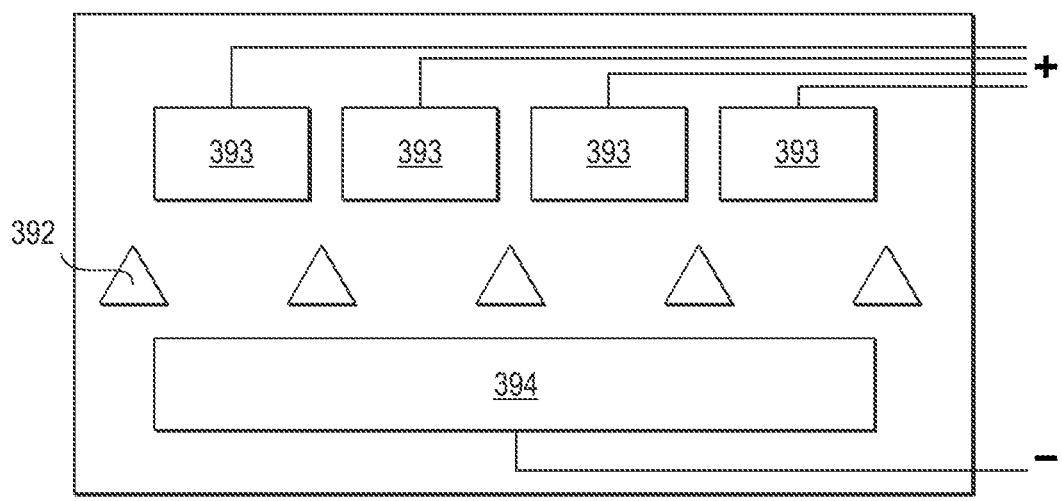

FIG. 16H illustrates a cross-sectional view of an electrode arrangement according to one embodiment. In some embodiments, the positive electrodes 393 of the array of electrodes may share a common negative electrode 394. Each RF output channel may include a positive electrode 393 and the negative electrode 394. While the negative electrode 394 is common, each positive electrode 393 may be independently controlled to achieve the desired treatment. In some embodiments, a temperature reading may be obtained from temperature input signals sensed from one or more thermocouples 392.

Figure 16I:
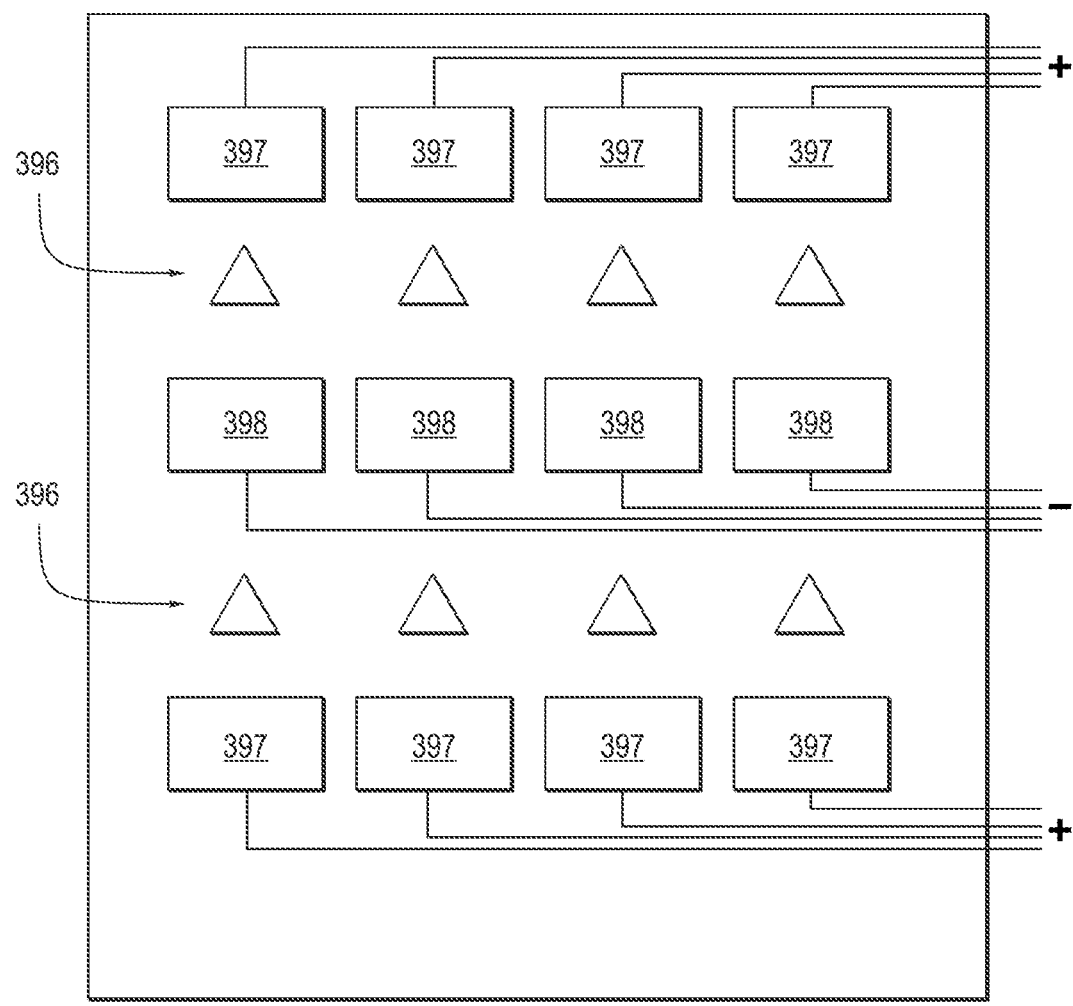

FIG. 16I illustrates a cross-sectional view of an electrode arrangement according to one embodiment. In this configuration there are two rows with the same polarity and a third row with a different polarity. For example, as shown in FIG. 16I, the outer rows of electrodes 397 have a positive polarity and the inner row of electrodes 398 has a negative polarity. Interspersed between the rows are a first and second row of thermocouples 396. This configuration may affect a larger area than other configurations.

Examples of Treatment Devices Including Electrodes

Embodiments of treatment devices incorporating treatment elements such as the electrodes described above are illustrated in FIGS. 17-19B. The designs described in these embodiments may be used in various devices, for example the device 30, described above. In certain embodiments, the devices provide tissue modification via energy delivery. Applying energy to the upper airway may require properly positioning the electrode(s) at the region to be treated, and delivering or applying energy consistently prior to device removal. Embodiments described herein may advantageously provide adjustability, visualization of effect, ease of use, ease of manufacturability and component cost.

Figure 17:
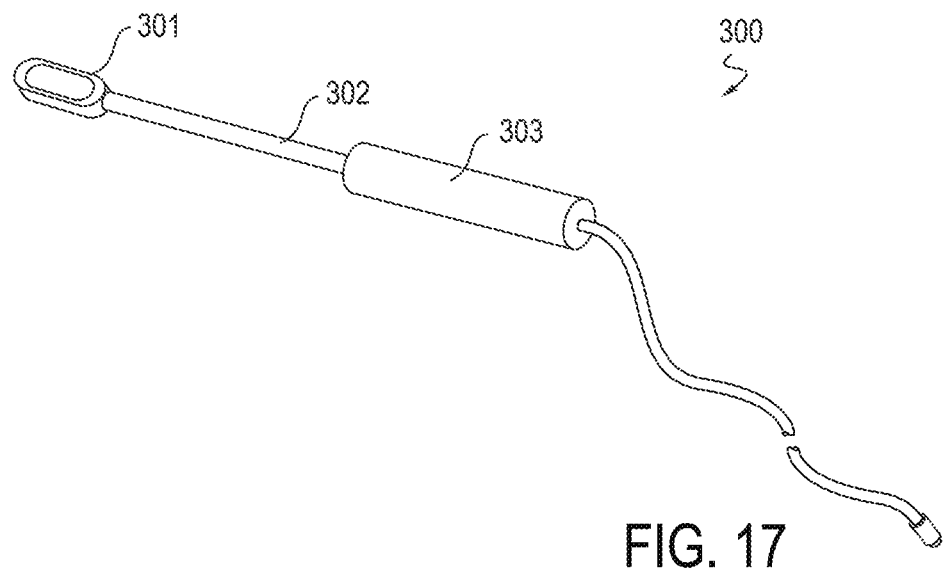
FIG. 17 is a perspective view of a device for applying energy to upper airway tissues using monopolar electrodes according to one embodiment.

FIG. 17 is a perspective view of a device 300 for applying energy to upper airway tissues using monopolar electrodes according to one embodiment. The device 300 may comprise a single inter-nasal monopolar electrode 301 located at the end of a shaft 302. A handle 303 may be attached to the shaft. In certain implementations, the electrode configuration may be similar to that described with respect to FIG. 12D.

Figure 18:
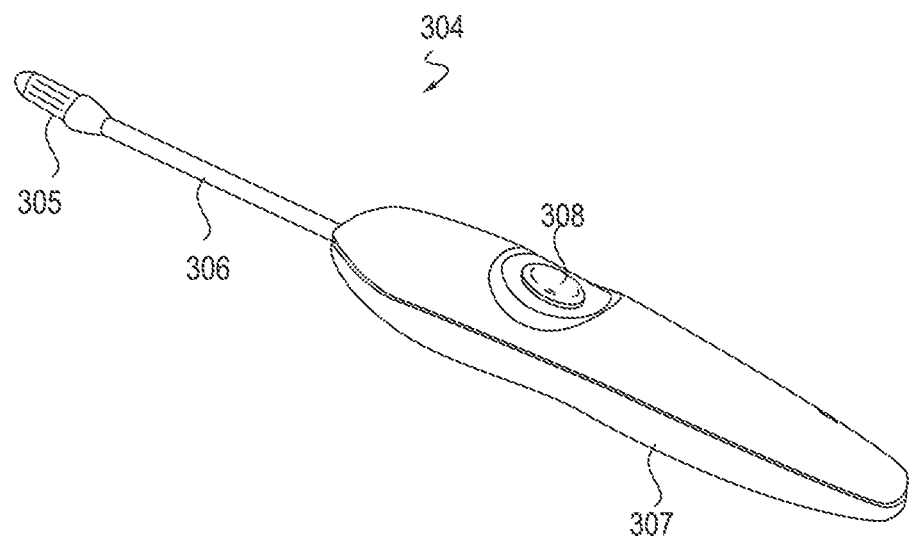
FIG. 18 is a perspective view of a device for applying energy to upper airway tissues using monopolar electrodes according to one embodiment.

FIG. 18 is a perspective view of a device 304 for applying energy to upper airway tissues using monopolar electrodes according to one embodiment. In certain implementations, the device 304 may comprise a single inter-nasal, monopolar electrode 305. The electrode 305 is located at the distal end of a shaft 306, which is attached to a handle 307. The handle 309 comprises a power button 308 that may be used to activate and deactivate the electrode. As stated above, the device 304 may either comprise a generator or be connected to a remote generator. The electrode 305 may be provided on an enlarged, distal end of the shaft 306.

Figure 19A:
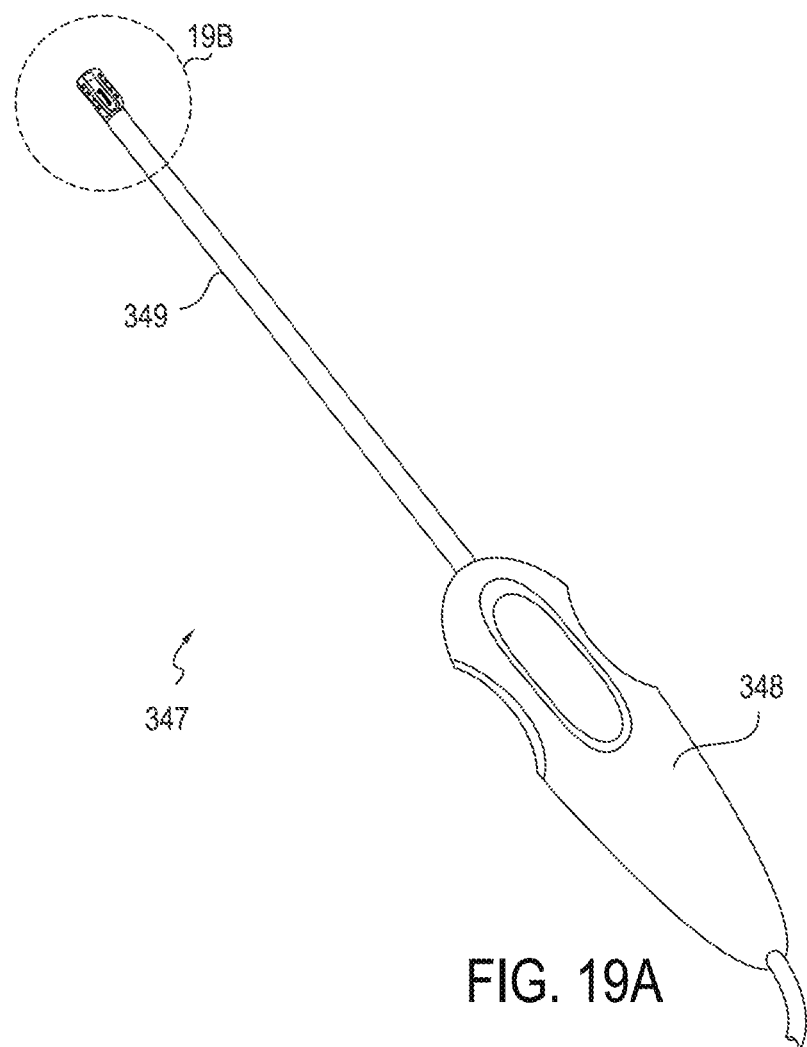
FIG. 19A is a perspective view of a device for applying energy to the upper airway tissues using a bipolar electrode according to one embodiment.
Figure 19B:
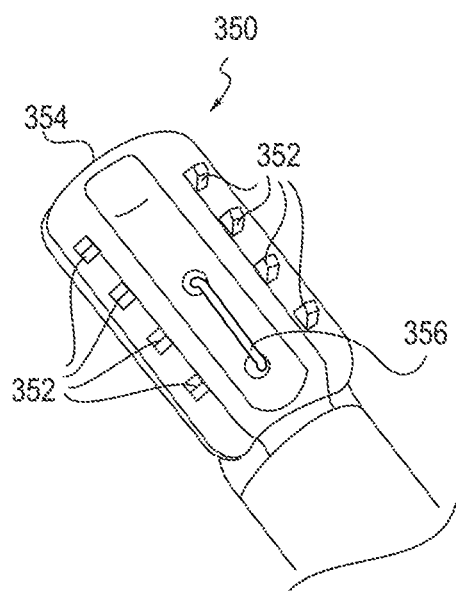
FIG. 19B is an enlarged perspective view of the treatment member of the device of FIG. 19A.

FIG. 19A is a perspective view of a device 347 for applying energy to the upper airway tissues using a bipolar electrode according to one embodiment. FIG. 19B illustrates an enlarged perspective view focusing on the treatment portion 350 of the device 347. In certain implementations, the device 347 may include a handle 348, a shaft 349, a treatment portion 350, radiofrequency electrodes 352 (such as bi-polar electrodes), a trough 354, and a thermocouple 356.

The handle 348 may be an area by which the device 347 may be held. The proximal end of the shaft 349 may be connected to the distal end of the handle 348.

The shaft 349 may be an elongate member extending from the handle 348. In certain implementations, the shaft 349 may be adjustable or otherwise malleable. For example, in certain implementations, the shaft 349 may be malleable or otherwise able to be formed into a particular shape and substantially retain the shape. The adjustability of the shaft 349 may enable a clinician to re-shape the shaft 349 to improve the ability of the device 347 to navigate nasal or other anatomy. The adjustability may also enable the electrodes 352 to be positioned to contact tissues to be treated.

The treatment portion 350 has tissue contact surface (or "treatment surface"), which is the surface of the treatment portion 350 that includes the multiple features for addressing and treating tissue, such as mucosal tissue. The treatment surface of the treatment portion 350 includes the concave-shaped trough 354 and two rows of electrodes 352 separated by the thermocouple 356, which is disposed within the trough 354. The electrodes 352 and the thermocouple 356 are both raised off of the treatment surface in this embodiment. However, other configurations are also possible (see, e.g., FIGS. 16A-I for other configurations of electrodes and thermocouples). In certain implementations, the treatment portion 350 may also be adjustable. For instance, the treatment portion 350 may be capable of being bent, twisted, rotated, flexed, or otherwise articulated to facilitate treatment.

In various alternative embodiments, the electrodes 352 may be replaced with any other suitable treatment delivery members. In various embodiments, for example, other forms of energy may be delivered by alternative energy delivery members. Such energy forms may include, but are not limited to, ultrasound, microwave, heat, radiofrequency, electrical, light and laser energy. In another alternative embodiment, energy may be removed from tissue by the treatment portion 350, via one or more cryotherapy members on the tissue contact surface. In yet other embodiments, the treatment portion 350 may include one or more substance delivery members. In certain implementations, the treatment portion 350 may be flush with the shaft 349, be an area of increased diameter of the shaft 349, or a combination thereof. In certain implementations, the treatment portion 350 may extend laterally from the distal end of the shaft 349.

The electrodes 352 may be recessed from, flush with, and/or protrude from the treatment portion 350. The electrodes 352 may extend substantially perpendicularly from the treatment portion 350 and/or may extend at a non-perpendicular angle. The rows of electrodes 352 may, but need not, extend parallel to each other. In certain implementations, one or more electrodes 352 may be designed to avoid puncturing tissue (e.g. by having blunt, rounded, or otherwise atraumatic tips). In certain other implementations, one or more electrodes 352 may be designed to puncture tissue.

The trough 354 may be an elongate, concave channel that runs substantially along the length of the treatment portion 350. In certain implementations, the trough 354 may be sized to or otherwise configured to match the size and/or shape of a nasal turbinate, such as the inferior nasal concha.

The thermocouple 356 may be one or more sensors configured to gather one or more temperature readings of tissue during operation of the device 347. In certain implementations, the thermocouple 356 may rest substantially flush with the trough 354. In certain other implementations, the thermocouple 356 may protrude from the trough 354. In certain embodiments, the protrusion may be slight, such that the thermocouple 356 remains within the trough 354, in other embodiments, the thermocouple 356 may extend out of the trough 354.

The electrodes 352 and the thermocouple 356 may be connected with a device control system connected integrated with or attached to the device 347. For example, the device 347 may comprise a generator or a means for connecting to a remote generator. This connection may be established through wires extending the length of the shaft 349 to a connection within a handle of the device 347.

Figure 20:
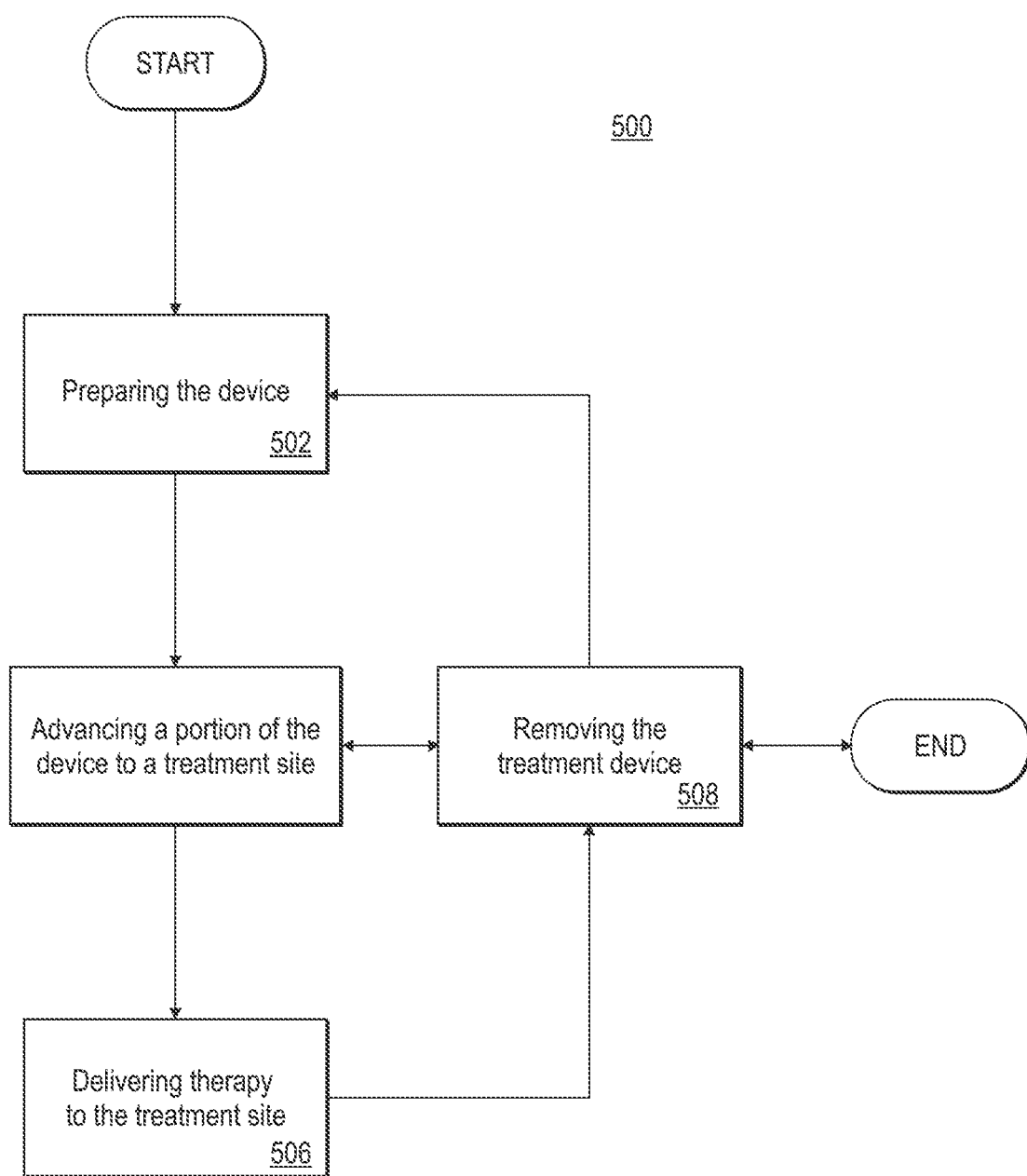
FIG. 20 is a flow diagram of an example method of use of various devices.

FIG. 20 is a flow diagram of an example method 500 of use of various devices, including the device 347. In certain implementations, the method 500 may include preparing the device 502, advancing a portion of the device to a treatment site 504, delivering therapy to the treatment site 506, and removing the treatment device 508.

In certain implementations, the method 500 may start at the step of preparing the device 502. Preparing the device 502 may include removing the device from sterile packaging, assembling one or more components of the device, sterilizing the device, attaching the device to an energy source, and/or other preparatory work. In certain implementations, this step may include customizing the device to suit the particular needs of the patient and the clinician. This may include articulating, manipulating, or otherwise changing one or more components of the device. For example, a clinician may articulate or bend the shaft 349 and/or the treatment portion 350 to place the device in a first, desired configuration. The first, desired configuration may be selected to facilitate navigation of the nasal anatomy of the particular patient to reach the desired treatment site.

In certain circumstances, preparing the device 502 may follow removing the treatment device 508. For example, the clinician may determine that the device is not suitable in its current state, remove the device, and then reconfigure the device in a more suitable format (e.g. a second configuration).

Advancing a portion of the device to a treatment site 504 may follow the preparation of the device 502. For example, the clinician may navigate the patient's nasal anatomy with the device 347 in the first configuration. Specifically, the clinician may advance a treatment portion of the treatment device into a nostril of the patient to contact a treatment surface of the treatment portion with mucosal tissue of the upper airway. This step 504 may be performed without piercing the mucosal tissue. The goal of the navigation may be to place the treatment element in contact with the treatment site.

In certain circumstances, advancing a portion of the device to a treatment site 504 may follow the removal of the treatment device 508. In this circumstance, this step may include the clinician wholly or partially re-navigating the device through the nasal anatomy to improve, for example, contact between the treatment portion 350 and the treatment site.

During navigation, the clinician may perform one or more tests to determine whether proper contact with the treatment site has been made. For example, the clinician may activate one or more pairs of the electrodes (such as electrodes 352). Based on measured results, the clinician may determine that proper contact has not been achieved because an energy pathway could not be made between one or more pairs of electrodes and/or that one or more measured electrical parameters (e.g., impedance, voltage, current, etc.) is outside of a desired range. As another example, the clinician may attempt to apply pressure to the treatment site with the treatment portion 350 and determine by feel whether proper contact has been made. As yet another example, the clinician may take a reading using a thermocouple (such as thermocouple 356) to determine whether proper contact has been made.

Based on the one or more tests, the clinician may determine that proper contact has been made between the treatment portion and the treatment site. In this situation, the flow may move to the step of delivering therapy to the treatment site 506. In certain circumstances, the clinician may determine that proper contact has not been made or that the device is otherwise unsuitable in its current state. In this situation, the flow may move to the step of removing the treatment device 508.

Delivering therapy to the treatment site 506 may follow advancing a portion of the device to a treatment site 504. In this step, the clinician may cause the device to apply energy to the treatment site. For example, in certain implementations, a clinician may use the device to apply energy to the posterior aspect of the inferior turbinate. For this treatment, it may be desirable to press the treatment portion against the tissue of the posterior aspect of the inferior turbinate such that the tissue substantially conforms to the shape of the treatment element.

For instance, a concave shape may be formed on the tissue turbinate against the convex shape of the treatment portion 350 of device 347. The electrodes 352 may create indentations within the tissue. A portion of the tissue may be enter and conform to the shape of the trough 354 and contact the thermocouple 356. While the tissue is in this configuration, the clinician may activate one or more pairs of electrodes 352 to deliver therapy to the treatment site. In certain implementations, delivering therapy to the treatment site 506 may include delivering radiofrequency energy from a first electrode on the treatment portion 350 across the trough 354 of the treatment portion 350 to a second electrode on the treatment portion 350, to treat at least one tissue selected from the group of the mucosal tissue and another tissue underlying the mucosal tissue to modify a property of the at least one tissue and thus treat at least one of post nasal drip or chronic cough in the patient.

The step of removing the treatment device 508 may follow from the step of advancing a portion of the device to a treatment site 504 and/or delivering therapy to the treatment site 506. In certain circumstances, the clinician may remove part or all of the device from the nasal anatomy of the patient. The clinician may determine that one or more further adjustments may improve contact between the treatment portion and the treatment site or otherwise achieve improved therapeutic results. In such circumstances, the flow may move to the step of preparing the device 502. For example, the clinician may articulate one or more components of the device to place the device in a second configuration. The clinician may then navigate the nasal anatomy again and deliver therapy to the treatment site.

When the step of removing the treatment device 508 follows from delivering therapy to the treatment site 506, the clinician may simply remove the device from the patient and end the procedure. In certain other circumstances, the clinician may partially or wholly remove the device and repeat one or more of the steps of the method 500 in order to more fully treat the treatment site and/or treat other treatment sites. In certain circumstances, the method 500 may end after step 508. While this method 500 has been described with reference to device 347, the method 500 may be used with some or all of the other devices and methods disclosed herein.

Figure 21A:
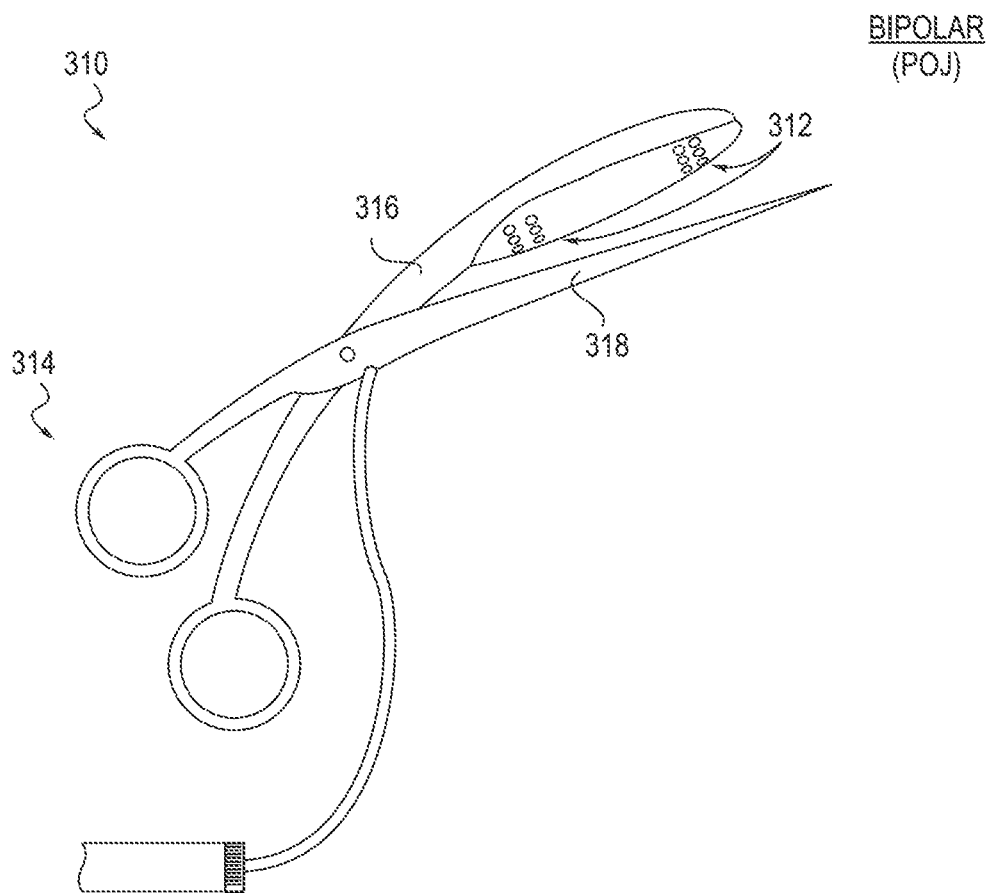
FIGS. 21A-21B are perspective views of a device for applying energy to the upper airway tissues using a bipolar electrode and a positioning element according to one embodiment.
Figure 21B:
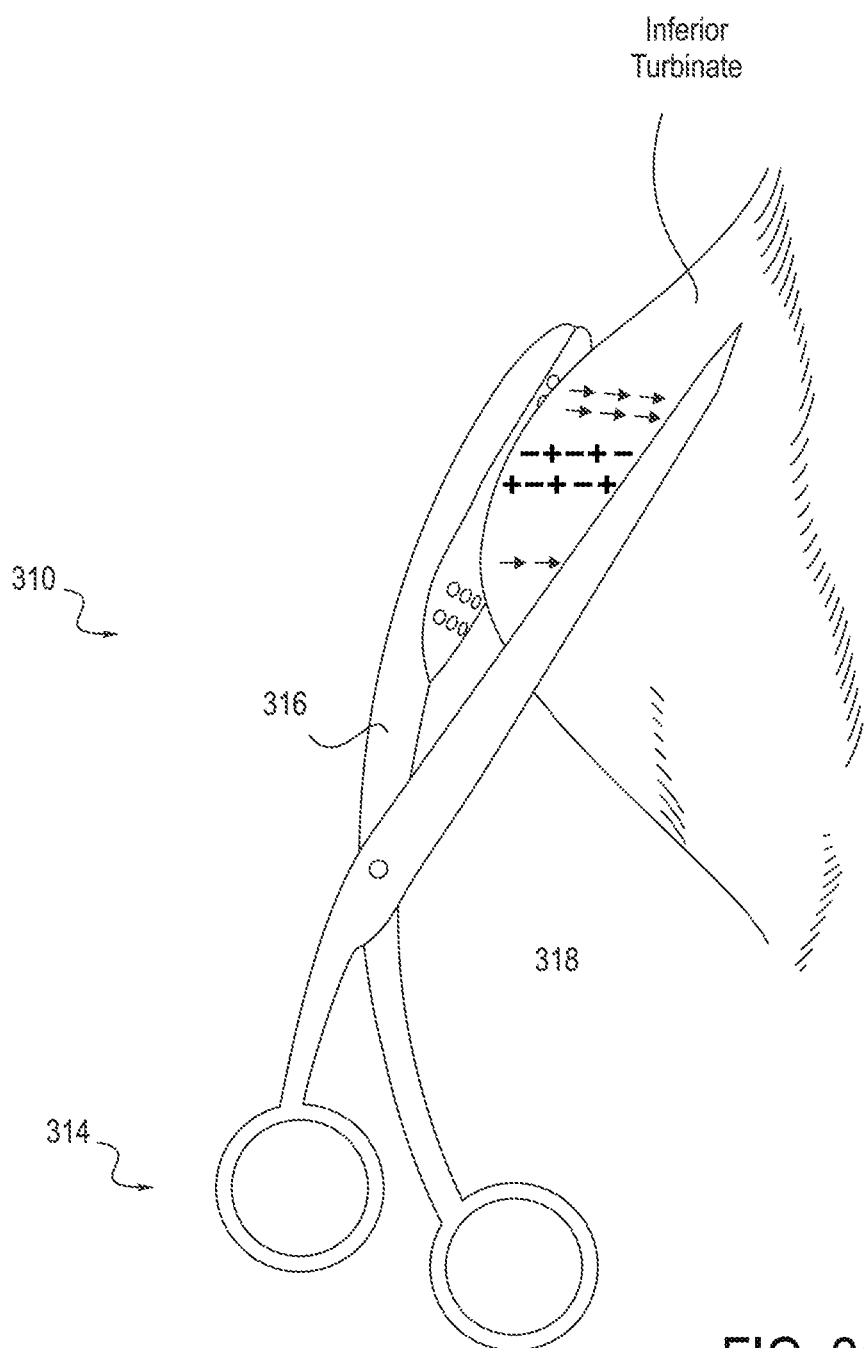

FIGS. 21A-B are perspective views of a device 310 for applying energy to the upper airway tissues using bipolar electrodes and a positioning element according to one embodiment. FIG. 21A depicts the device 310 comprising bipolar electrodes 312 located at the end of a shaft 316. The shaft 316 may be attached to a handle 314. Also attached to the handle 314 may be a grounding member 318. The shaft 316 and the grounding member 318 may be attached to the handle 314, such that one or both of the shaft 316 and the grounding member 318 may be moved relative to each other. In certain implementations, the grounding member 318 may be an external mold. The grounding probe 318 may be moved such that tissue to be treated is compressed between the grounding probe 318 and the electrode 312. In certain implementations, the grounding probe 318 may be a needle. The device 310 may be connected to a remote generator, or may comprise a generator. A power button on the handle 316 may be used to activate and deactivate the electrodes.

FIG. 21B illustrates the device 310 being used at an inferior turbinate. Specifically, the grounding member 318 pierces the tissue of the inferior turbinate and the bipolar electrodes 312 press against the tissue. When activated, current flows from one or more of the electrodes 312 to the grounding member 318.

Figure 22A:
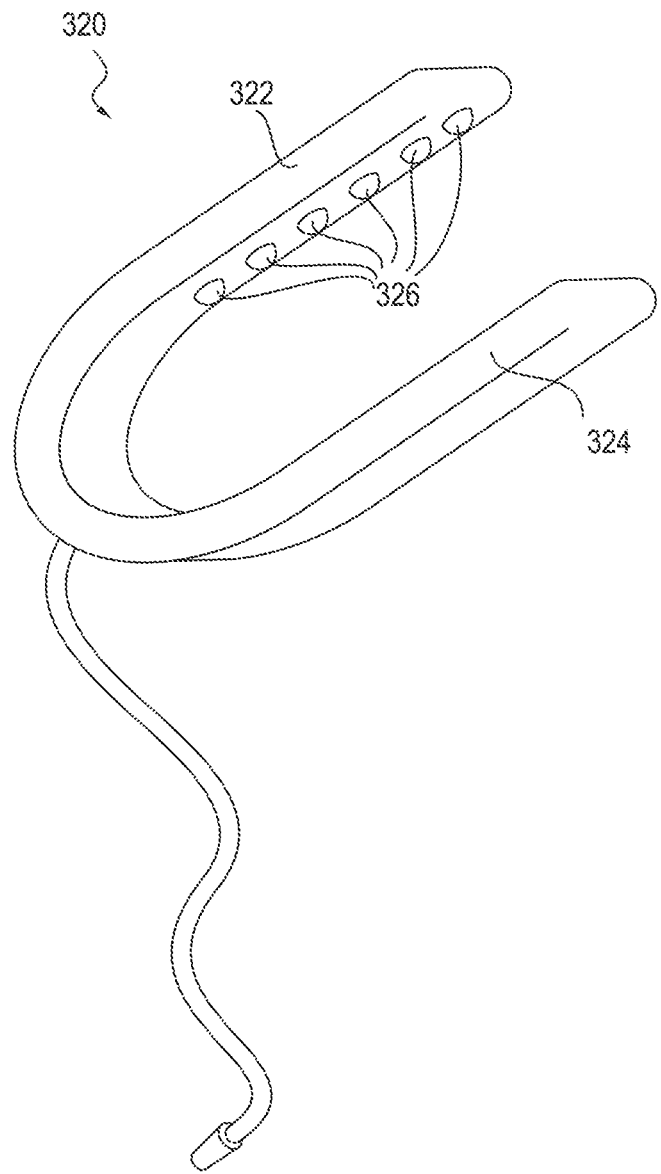
FIG. 22A is a perspective view of a clamp-like device for applying energy to the upper airway tissues using a bipolar electrode according to one embodiment.

FIG. 22A is a perspective view of a clamp-like device 320 for applying energy to the upper airway tissues using a bipolar electrode according to one embodiment. In certain implementations, the device 320 may comprise two prongs 322, 324. The prongs 322, 324 may be flexible such that they move towards each other when compressed by an external force, and upon removal of this force, they spring back to their original positions. Bipolar electrodes 326 may be located at the end of prong 322 while prong 324 acts as an external positioning element. Prongs 322 and 324 may be moved such that tissue to be treated is compressed between the prong 324 and the electrode 326. The device 320 may be connected to a remote generator, or the device may comprise a generator. A power button on one of the prongs 322, 324 or the junction between both prongs 322, 324 may be used to activate and deactivate the electrodes 326.

Figure 22B:
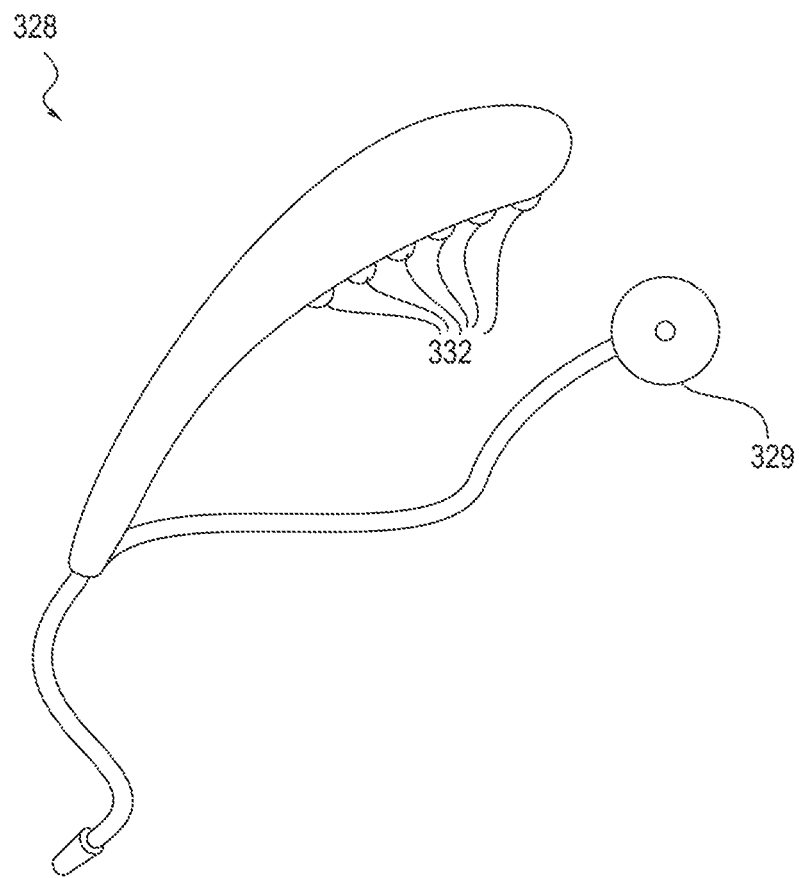
FIG. 22B is a perspective view of a one-prong device for applying energy to the upper airway tissues using a monopolar electrode according to one embodiment.

FIG. 22B is a perspective view of a one-prong device 328 for applying energy to the upper airway tissues using a monopolar electrode according to one embodiment. In certain implementations, the device 328 may comprise a single prong 330. Monopolar electrodes 332 may be located at the end of the prong 330. The prong 330 is inserted into the upper airway and electrodes 332 are placed on the tissue to be treated. A grounding pad 329 may be placed on the patient's body, usually the back. The device 328 may be connected to a remote generator, or it may comprise a generator, with a power button on the prong 330 that may be used to activate and deactivate the electrodes.

Figure 23:
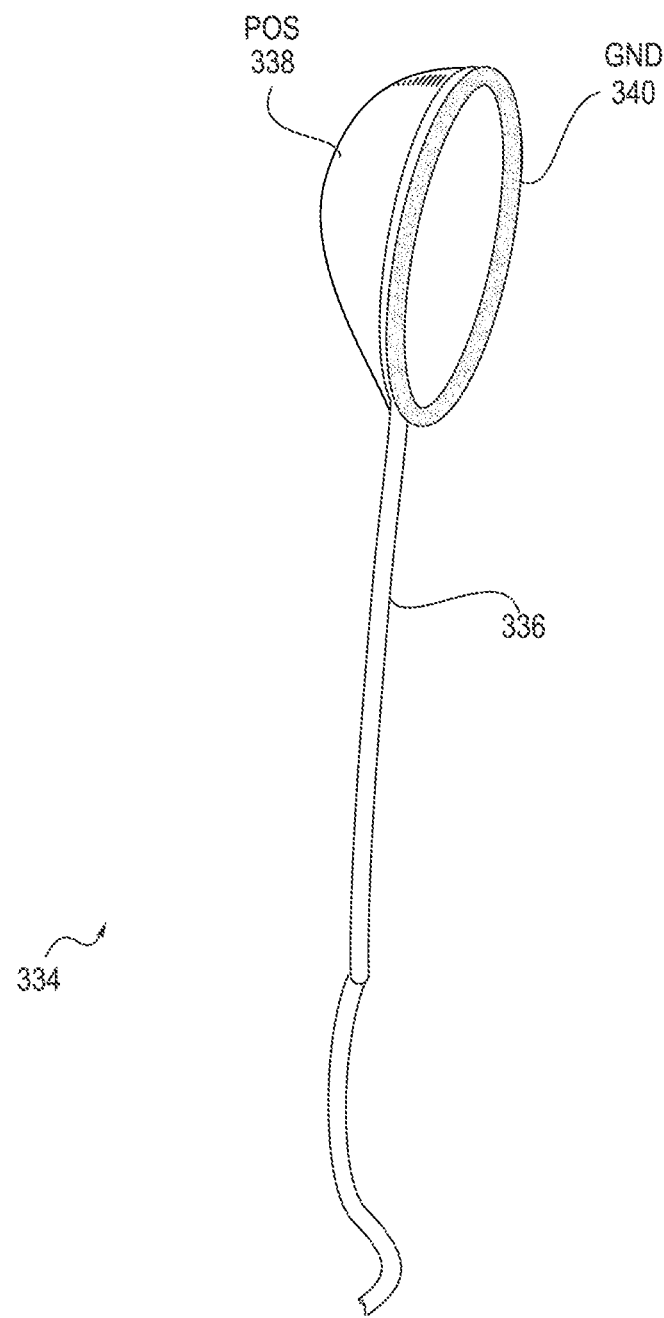
FIG. 23 is a perspective view of a device with concave head, for applying energy to the upper airway tissues using a bipolar electrode according to one embodiment.

FIG. 23 is a perspective view of a device 334 with concave head for applying energy to the upper airway tissues using a bipolar electrode according to one embodiment. In certain implementations, the device 334 may comprise bipolar electrodes located at the end of a shaft 336. The positive electrodes may be located on a concave surface 338 at the end of the shaft 336. A grounding ring 340 may be formed around the rim of the concave surface 338. The device 334 may be used to treat convex tissues with the tissues nestled within and compressed against the concave surface 338. The device 334 may be connected to a remote generator, or the device 334 may comprise a generator. A power button on shaft 336 may be used to activate and deactivate the electrodes. In certain implementations, the device 334 may be formed with a dome shape and have current passing from a top region to a bottom region. This may enable a maximum surface area of current flow.

Figure 24:
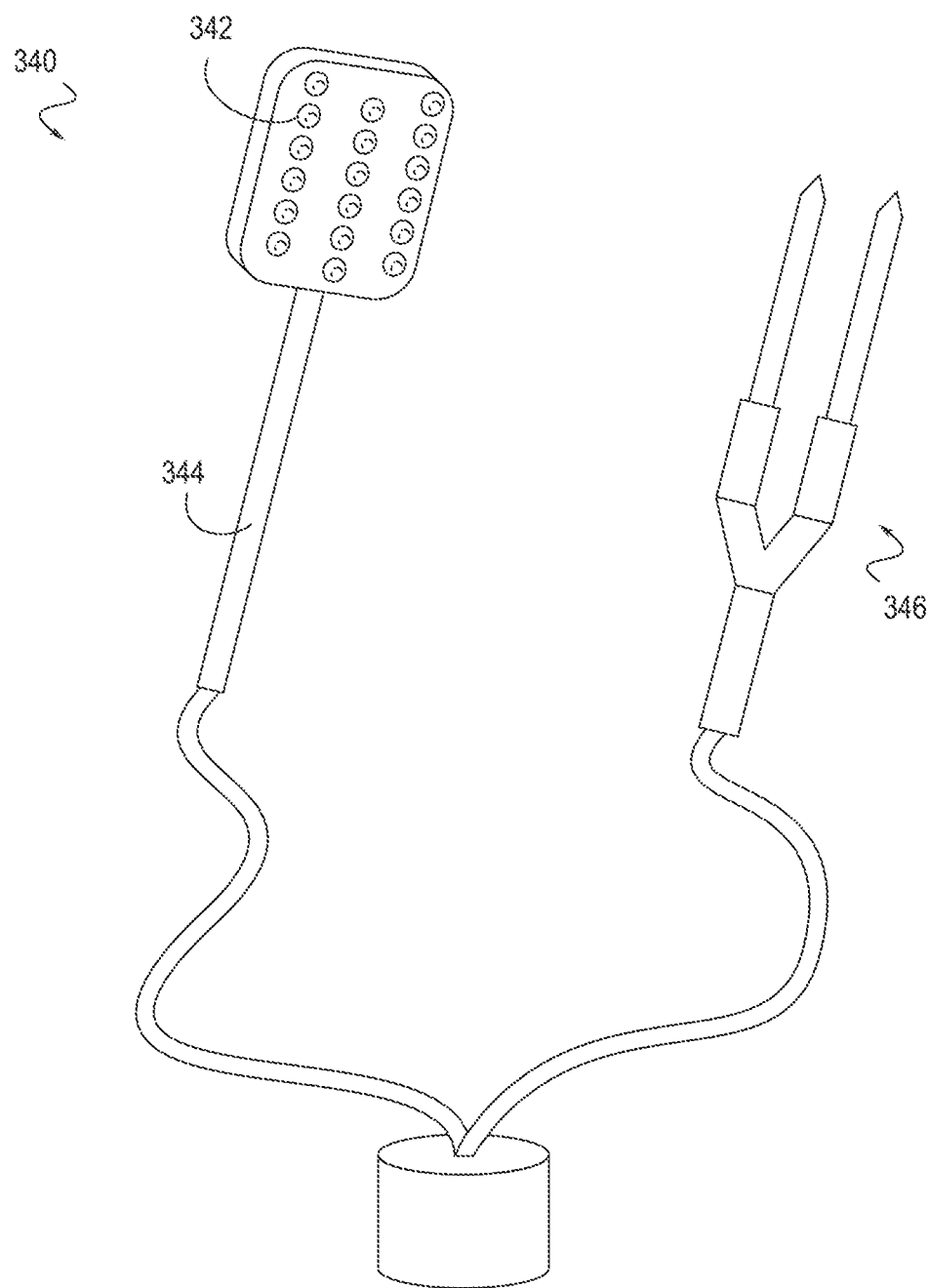
FIG. 24 is a perspective view of a device with grounding probes, for applying energy to the upper airway tissues using a monopolar electrode according to one embodiment.

FIG. 24 is a perspective view of a device 340 with grounding probes, for applying energy to the upper airway tissues using a monopolar electrode according to one embodiment. In certain implementations, the device 340 may comprise monopolar electrodes 342 located at the end of a shaft 344. The grounding probe 346 may be a needle or needles inserted into the tissue to be treated. The electrodes 342 may be compressed against the tissue to be treated. The device 340 may be connected to a remote generator, or it may comprise a generator, with a power button on shaft 344 that may be used to activate and deactivate the electrodes. It will be appreciated that any combination of electrode configurations, molds, handles, connection between handles, and the like may be used to treat the upper airway.

Profile of Treatment Element

The sizes and shapes of anatomies to be treated may vary at different treatment stages and also among different patients. To ensure best possible electrode-tissue contact, the treatment element 32 can be designed to be adjustable depending on the anatomy to be treated. Possible designs are mentioned below, it is also possible to have designs which are combinations of the ones mentioned. In certain implementations, the head may be designed with flexible wings, with electrodes of adjustable heights, and/or with one or more extensions.

Figure 25:
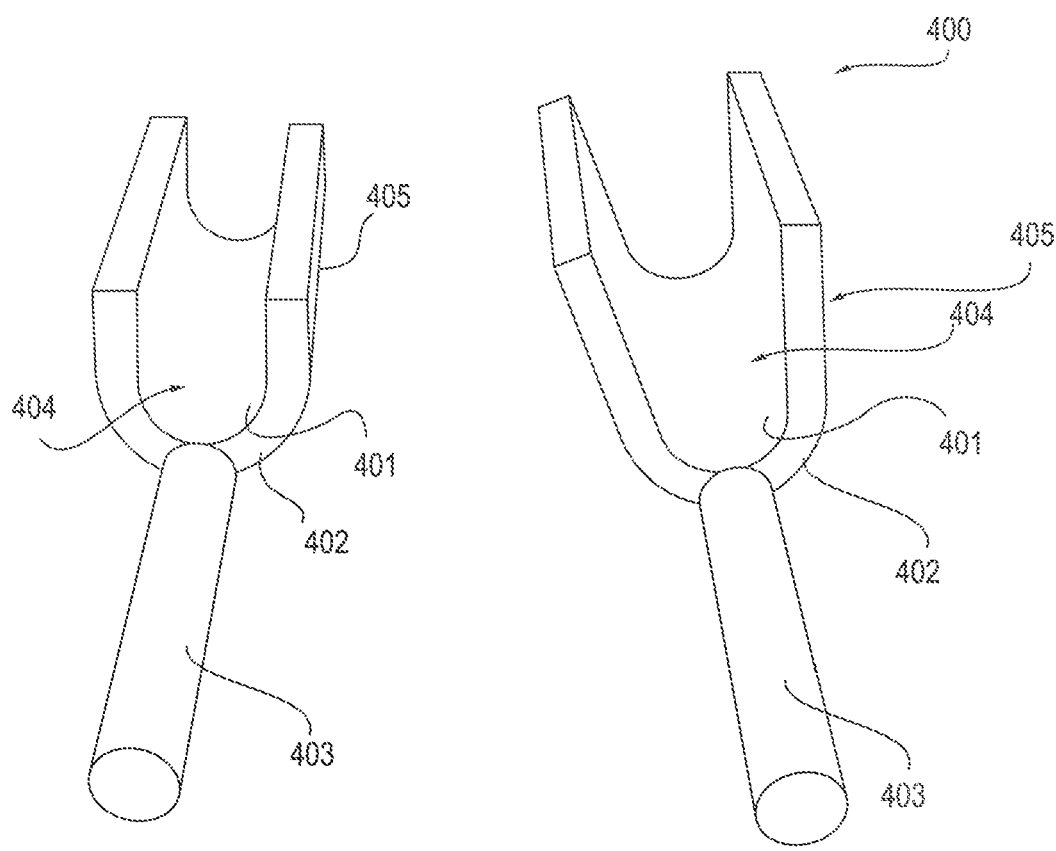
FIG. 25 is a perspective view of a treatment element with flexible wings according to one embodiment.

FIG. 25 is a perspective view of a treatment device 400 with flexible wings according to one embodiment. Electrodes may be positioned on the interior or exterior or both. In the case of a convex anatomy, the wings can be adjusted to wrap around the targeted anatomy, using the electrodes on the interior. In the case of a concave anatomy, the wings can be adjusted to fit into the anatomy, using the electrodes on the exterior.

In certain implementations, the device 400 may include a treatment element 401 positioned on a head section 402 of the device 400, which may be configured to be placed inside the nasal cavity, nasal passage, nasal airway, and/or other anatomy to deliver the desired treatment. The treatment element 401 may be positioned on an interior portion 404 and/or an exterior portion 405 of the head section 402. In some embodiments, the device 400 may further comprise a shaft section 403, which may be sized and configured for easy handheld operation by a clinician. In some embodiments, the head section 402 may be adjustable. It may be advantageous to use an adjustable head section 402 to treat anatomy that may vary in shape and size. The shape of the head section 402 or parts of the head section 402 may be actively or passively adjusted to affect the engagement to the tissue or the effect on the tissue. In some embodiments, the adjustment of the head section 402 may result in a change in shape and/or size of the interior portion 404 and/or the exterior portion 405.

The head section 402 may be implemented using flexible sections configured to be adjusted depending on the anatomy to be treated. Electrodes (not shown) may be positioned on the interior or the exterior of the flexible sections. In some embodiments, electrodes may be positioned on both the interior 404 and the exterior 405 of the flexible sections. For example, in the case of a convex anatomy, the flexible sections may be adjusted to wrap around the anatomy using electrodes on the interior 404 of the flexible sections. In the case of a concave anatomy, the flexible sections may be adjusted to fit into the anatomy using electrodes on the exterior 405 of the flexible sections. In some embodiments, the head section 402 may include functionality to inflate and deflate the flexible sections to adjust the size of a treatment surface of the device 400 in a radial direction. In some embodiments, the head section 402 may include functionality to rotate the head section 402 in any direction to allow the head section 402 to be angled in a desired position.

FIGS. 26A-F are perspective views of embodiments of the treatment device 400 with an electrode array 410 having adjustable heights. In some implementations, one or more electrodes of the electrode array 410 may have adjustable heights. For example, each electrode may extend or retract to a preset height, achieving a combination which forms the required treatment surface profile. The surface profile may be in any combination of electrode heights.

In certain implementations, the electrode array 410 may include numerous electrodes positioned on a surface of a treatment element 401 of the device 400. In some embodiments, the electrodes may be arranged in a grid pattern. The electrodes may be arranged in any pattern. One or more of the electrodes may be extended or retracted to a preset height. It may be advantageous to manipulate the heights of the electrodes of the electrode array 410 to achieve a combination that forms a required treatment surface profile 411. The treatment surface profile 411 may include any combination of electrode numbers and heights. For example, the electrodes may be arranged and manipulated to achieve a generally concave treatment surface profile, a generally convex treatment surface profile (see, e.g., FIG. 26F and FIG. 26C), a generally flat treatment surface profile (See, e.g., FIG. 26E and FIG. 26B), and/or a generally concave treatment surface profile (see, e.g., FIG. 26D and FIG. 26A).

Figure 27:
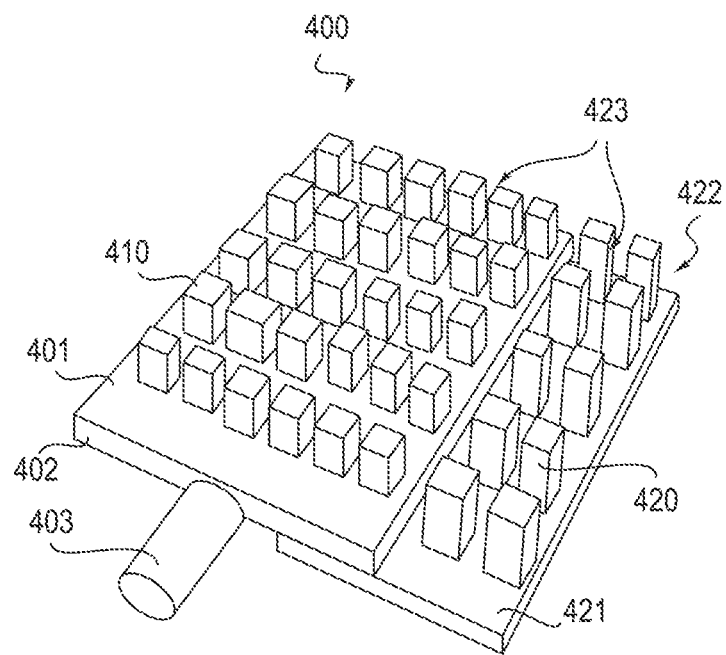
FIG. 27 is a perspective view of a treatment element with an extendable component according to one embodiment.

FIG. 27 is a perspective view of an embodiment of the treatment device 400 with an extendable component 422. The expandable component 422 may be used to adjust the size of the treatment surface of the treatment device 400. The extendable component 422 may be moved in any direction, not limited to the direction shown in FIG. 27. The number of extendable components 422 need not be limited to one.

In certain implementations, an embodiment of a nasal valve treatment device 400, comprising a first treatment element 401 and a second treatment element 421. The first treatment element 401 may be positioned on a first side of a head section 402. The first treatment element 401 may include a first electrode array 410. In some embodiments, the head section 402 may be implemented with an extendable component 422. It may be advantageous to provide an extendable component 422 to allow the size of the treatment surface 423 to be adjustable. The extendable component 422 may include a second treatment element 421, including a second electrode array 420. In some embodiments, the extendable component 422 may be positioned on a second side of the head section 402 such that it is behind the first treatment element 401. The extendable component 422 may include functionality to move such that it may be shifted from behind the first treatment element 401 of the head section 402 to adjacent to the first treatment element 401 of the head section 402. This shift may expose the second electrode array 420, thereby extending the treatment surface 423. The extendable component 422 may be moved in any direction, and the direction depicted in FIG. 27 is merely an example of one direction in which it may be moved. All adjustments can be applied before and also during treatments so as to cater to anatomy changes during treatments.

FIGS. 28A-E are side-cutaway views of treatment elements according to certain embodiments. The treatment elements may be configured to maintain different temperatures in adjacent tissues. Differential cooling mechanisms may be applied to a cross-section of tissue.

Figure 28A:
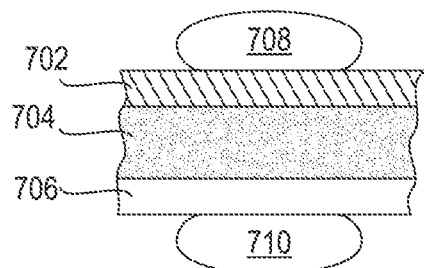
FIGS. 28A-28E are side-cutaway views of treatment elements according to certain embodiments.

As shown in FIG. 28A, in some embodiments, the differential cooling mechanism comprises two elements: a first element 708 and a second element 710. The two elements are on either side of the thickness of the nasal tissue. In one embodiment, the mechanism is configured to maintain normal temperatures in the cartilage 704 while cooling the mucosa 702 and the skin 706. In such an embodiment, the first and second elements 708, 710 comprise a cooling apparatus such as those described above (e.g., heat sink, coolant lines, etc.). In some embodiments, the mucosa 702 and the skin 706 are heated while normal temperatures are maintained in the cartilaginous middle layer 704. The cartilage 704 may be somewhat warmed, in such embodiments, but may be cooler than the mucosa 702 and the skin 706. In such embodiments, the first and second elements 708, 710 comprise a heating apparatus, such as radio frequency electrodes or resistive heating elements. Depending on the treatment target, the temperature of different layers or regions of tissue may be controlled. For example, in some embodiments, the mucosa 702 is heated, the skin 706 is cooled, and normal temperatures are maintained in the cartilage 704. In such embodiments, the first element 708 comprises a heating apparatus and the second element 710 comprises a cooling apparatus. As another example, in some embodiments, the skin 706 is heated, the mucosa 702 is cooled, and normal temperatures are maintained in the cartilage 704. In such embodiments, the first element 708 comprises a cooling apparatus and the second element 710 comprises a heating apparatus. As another example, submucosa and associated cells are heated while normal temperatures are maintained elsewhere.

Figure 28B:
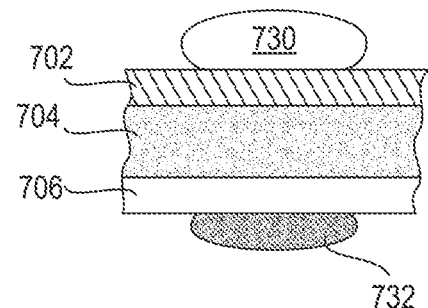

FIG. 28B shows an example of one of the embodiments described with respect to FIG. 28A. The first element 730 is on the mucosal surface 702. The second element 732 is an energy delivery element and is positioned on the skin side 706 of the tissue thickness. The first element 730 comprises a cooling apparatus and the second element 732 comprises an energy delivery element (e.g., an RF electrode). The mucosal layer 702 is cooled while the skin 706 and cartilaginous areas 704 are heated. In other embodiments, the first element 730 can be positioned on the skin 706 and the second element 732 can be positioned on the mucosa 702. In such embodiments, the skin 706 is cooled while the mucosa 702 and the cartilage 704 are heated.

Figure 28C:
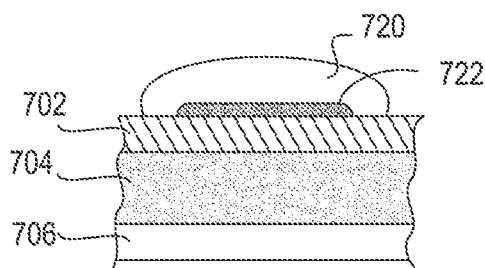

As shown in FIG. 28C, in some embodiments, the differential cooling mechanism comprises a first element 720 and a second element 722. Both elements 720, 722 are on the mucosa 702 side of the tissue thickness. In some embodiments, the mucosal layer 702 is cooled while higher temperatures are maintained in the middle cartilaginous layer 704. In such embodiments, the first element 720 comprises a cooling apparatus, and the second element 722 comprises an energy delivery apparatus (e.g., a monopolar radiofrequency electrode). In some embodiments, the first element 720 is sufficiently efficient to maintain cool temperatures at the mucosa 702 despite the energy provided by the second element 722. In other embodiments, the first and second elements 720, 722 are both positioned on the skin side 706 of the tissue thickness. In such embodiments, the skin 706 is cooled while higher temperatures are maintained in the middle cartilaginous layer.

Figure 28D:
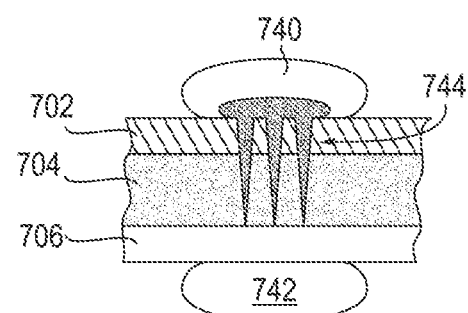

As shown in FIG. 28D, in some embodiments, the differential cooling mechanism comprises a first surface element 740 and a second surface element 742 on either side of the tissue thickness. A third subsurface element 744 is engaged through the mucosa 702 and into the cartilage area 704. In some embodiments, the mucosa 702 and the skin 706 are cooled while the middle cartilaginous layer 704 is heated. In such embodiments, the first and second elements 740, 742 comprise cooling apparatus while the third element 744 comprises a heating element (e.g., RF monopolar electrode, RF bipolar needles, etc.). In other embodiments, the third subsurface element 744 may be engaged through the skin 706 and into the cartilage area 704.

Figure 28E:
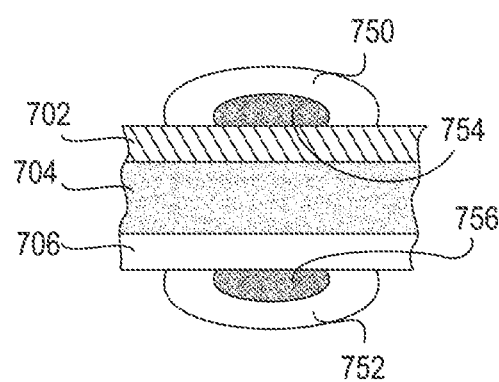

As shown in FIG. 28E, in some embodiments, the differential cooling mechanism comprises a first surface element 750 and a second surface element 752 on either side of the tissue thickness. The differential cooling mechanism further comprises a third surface element 754 and a fourth surface element 756 on either side of the tissue thickness. In some embodiments, the cartilage layer 704 is heated while the mucosa 702 and the skin 706 are cooled. In such embodiments, the first and second elements 750, 752 comprise cooling apparatus and the third and fourth elements 754, 756 comprise energy delivery apparatuses (e.g., bipolar plate electrodes). In some embodiments, the cartilage 704 and mucosal 702 layers are heated while the skin 706 is cooled. In such embodiments, the first element 750 comprises a heating apparatus; the second element 752 comprises a cooling apparatus; and the third and fourth elements 754, 756 comprise energy delivery apparatuses. It will be appreciated that different differential temperature effects can be achieved by reconfiguring and adding or subtracting to the described configuration of elements.

Figure 29A:
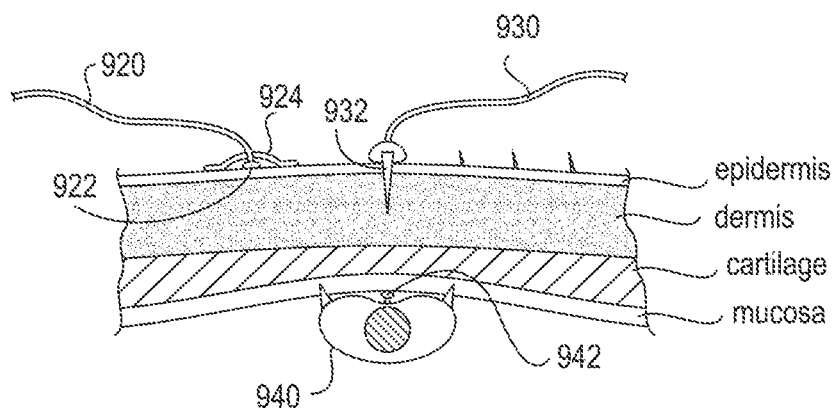
FIG. 29A is a side-cutaway view of nasal skin in cross section, including mucosa, cartilage, dermis and epidermis and a treatment device having an external component according to one embodiment.
Figure 29B:
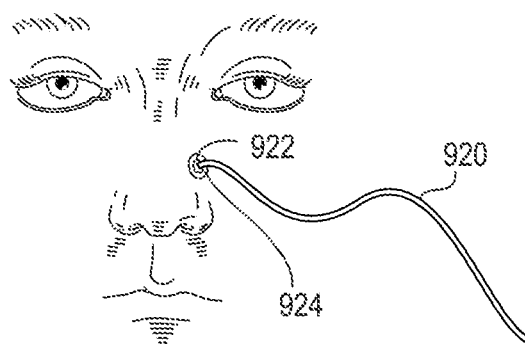
FIG. 29B is a perspective view of a treatment of an applied external component according to one embodiment.

FIGS. 29A-B illustrate certain implementations of a system for treating a nasal airway including one or more sensors. Such sensors may be used to sense any of a number of relevant tissue properties, such as temperature, impedance and the like. The sensors may be located on a treatment device in some embodiments, or alternatively they may be separate from the treatment device and positioned at or near the device during treatment. In some embodiments, the sensor(s) may provide feedback directly to the treatment device. For example if a particular tissue temperature threshold is reached, a sensor (or sensors) may send a signal to a power generator to shut down or decrease power delivered to a treatment device. In alternative embodiment, the sensor(s) may instead provide feedback to a physician or other user, so that the physician or other user can make treatment adjustments. For example, sensors may provide a warning signal when a particular tissue temperature or impedance is reached, which will help a physician know when to turn off or decrease power delivery to a treatment device. Additionally, sensor(s) may be used to sense one or more tissue properties in any suitable tissue or multiple tissues, such as but not limited to mucosa, cartilage, dermis, epidermis and other types of body soft tissue.

FIG. 29A is a side-cutaway view of nasal skin in cross section, including mucosa, cartilage, dermis and epidermis and a treatment device having an external component according to one embodiment. In certain implementations, a sensor device 920 may include an epidermal sensor 922 that is coupled to the epidermis via an adhesive 924. Any suitable sensor 922 (temperature, impedance, etc.) and any suitable adhesive 924 may be used. This embodiment of the sensor device 920 is also illustrated on a patient's face in FIG. 29B.

In an alternative embodiment, a sensor device 930 may include a transdermal needle sensor 932. In another alternative embodiment, a sensor device 942 may be attached directly to a treatment device 940. As illustrated by these various embodiments, sensors 922, 932 and 942 may be positioned either at or near a treatment location during a treatment. In some embodiments, for example, a sensor 922, 932 may be placed on or in epidermis while a treatment is being performed on mucosa. Alternatively, a sensor 942 may be placed directly on mucosa during a treatment of mucosa. Additionally, in any given embodiment, multiple sensors may be placed at multiple different locations in and/or on tissue. As mentioned above, the sensor devices 920, 930 and 940 may, in various embodiments, provide any of a number of different types of feedback, such as feedback to a user, feedback to a power generator, or both.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method for treating a nasal cavity of a patient by deactivating nerve tissue without forming an incision or implanting an implant, the method comprising:
    advancing a treatment element of a treatment device into a nostril of the patient;
    expanding multiple pre-shaped segments of the treatment element to cause them to contact mucosa lining the nasal cavity; and
    delivering radiofrequency energy through the mucosa with at least a first pair of bipolar radiofrequency electrodes on at least two of the pre-shaped segments, while leaving at least a second pair of bipolar radiofrequency electrodes on the pre-shaped segments in an inactive state,
    wherein delivering the radiofrequency energy with at least the first pair of bipolar radiofrequency electrodes deactivates the nerve tissue underlying the mucosa.

2. The method of claim 1, wherein delivering the radiofrequency energy ablates the nerve tissue.

3. The method of claim 1, wherein expanding the pre-shaped segments comprises by exposing them to a change of temperature past a transition temperature.

4. The method of claim 1, further comprising using a control system coupled with the treatment device to select at least the first pair of bipolar radiofrequency electrodes for delivering the radiofrequency energy and to select at least the second pair of bipolar radiofrequency electrodes for maintaining in the inactive state.

5. The method of claim 4, further comprising measuring impedance with an impedance sensor in the control system.

6. The method of claim 5, wherein measuring the impedance comprises:
    activating at least the first pair of bipolar radiofrequency electrodes and the second pair of bipolar radiofrequency electrodes;
    measuring a first impedance in the first pair of bipolar radiofrequency electrodes; and
    measuring a second impedance in the second pair of bipolar radiofrequency electrodes.

7. The method of claim 6, further comprising:
    determining, with the controller, that the second impedance is outside a desired range.

8. The method of claim 1, further comprising sensing a temperature of the mucosa with at least one thermocouple attached to at least one of the pre-shaped segments.

9. The method of claim 1, further comprising determining that the patient has a nasal mucus hypersecretion condition, wherein deactivating the nerve tissue ameliorates at least one symptom of the nasal mucus hypersecretion condition.

10. A system for treating a nasal cavity of a patient without forming an incision or implanting an implant, the system comprising:
  a treatment device, comprising:
    a handle;
    a shaft extending from the handle; and
    a treatment element coupled with a distal end of the shaft and sized to allow it to pass into the nasal cavity of the patient, wherein the treatment element comprises:
      multiple pre-shaped expandable segments; and
      multiple pairs of bipolar radiofrequency electrodes disposed on the multiple pre-shaped expandable segments;
  a control system coupled with the treatment device, comprising:
    a generator for providing radiofrequency energy to the multiple pairs of bipolar radiofrequency electrodes; and
    an impedance sensor for sensing impedance between the multiple pairs of bipolar radiofrequency electrodes.

11. The system of claim 10, wherein the multiple pre-shaped expandable segments are made of a shape-memory material selected from the group consisting of nickel-cobalt, nickel-titanium, shape memory polymers, and biodegradable polymers.

* * * * *